US012428511B2

United States Patent
Shiraiwa et al.

(10) Patent No.: US 12,428,511 B2
(45) Date of Patent: Sep. 30, 2025

(54) RESIN COMPOSITION, CURED PRODUCT, DIFFRACTIVE OPTICAL ELEMENT, AND MULTILAYER DIFFRACTIVE OPTICAL ELEMENT

(71) Applicant: FUJIFILM Corporation, Tokyo (JP)

(72) Inventors: Naozumi Shiraiwa, Ashigarakami-gun (JP); Takayasu Nagai, Ashigarakami-gun (JP); Naoyuki Morooka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1033 days.

(21) Appl. No.: 17/396,058

(22) Filed: Aug. 6, 2021

(65) Prior Publication Data

US 2021/0395418 A1 Dec. 23, 2021

Related U.S. Application Data

(63) Continuation of application No. PCT/JP2020/006987, filed on Feb. 21, 2020.

(30) Foreign Application Priority Data

Feb. 22, 2019 (JP) ................................ 2019-030490

(51) Int. Cl.
*C08F 222/10* (2006.01)
*C07D 339/06* (2006.01)
(Continued)

(52) U.S. Cl.
CPC ........ *C08F 222/102* (2020.02); *C07D 339/06* (2013.01); *C08F 222/24* (2013.01);
(Continued)

(58) Field of Classification Search
CPC .......................... C08F 222/24; C08F 222/102; C08F 2800/20; C08K 3/22; C08K 2003/2231;
(Continued)

(56) References Cited

U.S. PATENT DOCUMENTS

| 2009/0080093 A1* | 3/2009 | Ning ...................... G02B 13/04 359/753 |
| 2013/0224476 A1* | 8/2013 | Zheng .................. C09D 183/06 977/773 |

(Continued)

FOREIGN PATENT DOCUMENTS

| JP | 2006-220689 A | 8/2006 |
| JP | 2015-143787 A | 8/2015 |

(Continued)

OTHER PUBLICATIONS

International Search Report dated May 19, 2020 from the International Searching Authority in International Application No. PCT/JP2020/006987.

(Continued)

*Primary Examiner* — Bijan Ahvazi
(74) *Attorney, Agent, or Firm* — Sughrue Mion, PLLC

(57) ABSTRACT

The present invention provides a resin composition suitable for producing a diffractive optical element, the resin composition including an indium tin oxide particle and a near-ultraviolet light-absorbing organic compound having a maximum value of an absorbance at 340 nm to 400 nm in an absorption spectrum in a wavelength region of 300 nm to 780 nm and exhibiting substantially no light absorption at a wavelength of 410 to 800 nm.

19 Claims, 1 Drawing Sheet

(51) Int. Cl.
*C08F 222/24* (2006.01)
*C08K 3/22* (2006.01)
*G02B 1/04* (2006.01)
*G02B 5/18* (2006.01)

(52) U.S. Cl.
CPC ............. *C08K 3/22* (2013.01); *G02B 1/04* (2013.01); *G02B 5/1814* (2013.01); *G02B 5/1866* (2013.01); *C08F 2800/20* (2013.01); *C08K 2003/2231* (2013.01)

(58) Field of Classification Search
CPC ...... C07D 339/06; G02B 1/04; G02B 5/1814; G02B 5/1866
See application file for complete search history.

(56) References Cited

U.S. PATENT DOCUMENTS

| | | | |
|---|---|---|---|
| 2016/0077251 A1* | 3/2016 | Genda | G02B 5/189 359/576 |
| 2018/0362847 A1 | 12/2018 | Saito et al. | |
| 2020/0199095 A1* | 6/2020 | Morooka | C08F 222/1025 |

FOREIGN PATENT DOCUMENTS

| | | |
|---|---|---|
| WO | 2017/098988 A1 | 6/2017 |
| WO | 2018/116836 A1 | 6/2018 |
| WO | 2018/123705 A1 | 7/2018 |
| WO | 2019/044863 A1 | 3/2019 |

OTHER PUBLICATIONS

Written Opinion dated May 19, 2020 from the International Searching Authority in International Application No. PCT/JP2020/006987.
International Preliminary Report on Patentability with the translation of Written Opinion dated Aug. 10, 2021 from the International Bureau in International Application No. PCT/JP2020/006987.
Office Action dated Jun. 7, 2022, issued in Japanese Application No. 2021-502172.

* cited by examiner

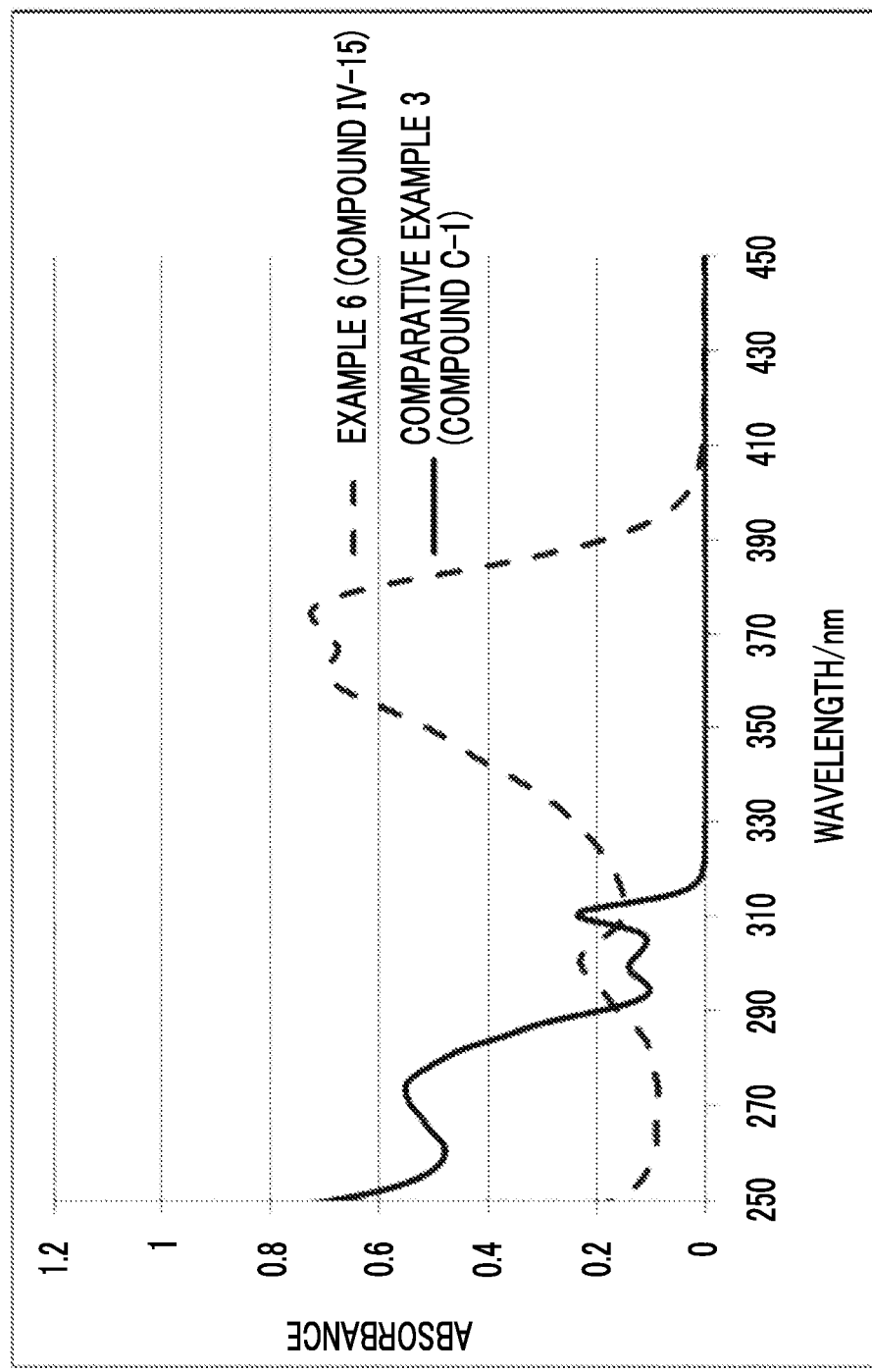

RESIN COMPOSITION, CURED PRODUCT, DIFFRACTIVE OPTICAL ELEMENT, AND MULTILAYER DIFFRACTIVE OPTICAL ELEMENT

CROSS-REFERENCE TO RELATED APPLICATIONS

This application is a continuation of PCT International Application No. PCT/JP2020/006987 filed on Feb. 21, 2020, which claims priority under 35 U.S.C § 119 (a) to Japanese Patent Application No, 2019-030490 filed on Feb. 22, 2019, the entire content of which is incorporated herein by reference.

BACKGROUND OF THE INVENTION

1. Field of the Invention

The present invention relates to a resin composition. The present invention particularly relates to a resin composition including ITO particles. The present invention also relates to a cured product obtained using the resin composition, a diffractive optical element, and a multilayer diffractive optical element.

2. Description of the Related Art

By using a diffractive optical element, it is possible to obtain a lens which has a shorter focal length as the wavelength is longer, and exhibits chromatic aberration opposite to that of a refractive lens in the related art. Unlike the refractive lens requiring a plurality of lenses for correcting chromatic aberration, chromatic aberration can be corrected by changing the period of a diffraction structure of a lens, therefore a more compact and high-performance lens unit can be designed by using the diffractive optical element.

In a multilayer diffractive optical element having a structure in which diffractive optical elements formed of two different materials are in contact with each other on lattice planes thereof, by forming one diffractive optical element with a material having a relatively high refractive index and high Abbe number, and forming the other diffractive optical element with a material having a relatively low refractive index and low Abbe number, it is possible to suppress the occurrence of flare in the lens, and the like, and sufficiently utilize a chromatic aberration reducing effect. In this case, in a case where the two diffractive optical elements have optical characteristics in which the difference in refractive index between the two diffractive optical elements is larger at a longer wavelength, the chromatic aberration reducing effect can be obtained in a wide wavelength range.

In recent years, in order to obtain, as described above, the chromatic aberration reducing effect in a wide wavelength range, it has been proposed to add indium tin oxide (ITO) particles to a curable resin composition which is used as a material for producing a low Abbe number diffractive optical element in the multilayer diffractive optical element. For example, JP2006-220689A discloses, as a curable resin composition for producing a diffractive optical element, a curable resin composition in which ITO fine particles are dispersed in a resin containing a photopolymerization initiator, a dispersant, and a mixture of two or more acryloyl groups, methacryloyl groups, or vinyl groups, or unsaturated ethylene groups thereof.

SUMMARY OF THE INVENTION

In the technique disclosed in JP2006-220689A, by adding ITO particles, the refractive index of the cured product obtained from the curable resin composition in the near-infrared wavelength region is lowered, and the chromatic aberration reducing effect is improved. However, in an optical system which uses light in the near-infrared wavelength region, it has been found that the decrease in transmittance in the near-infrared wavelength region due to the addition of ITO particles is a problem.

An object of the present invention is to provide a resin composition suitable for producing a diffractive optical element. More specifically, an object of the present invention is to provide a resin composition including ITO particles, in which the resin composition has high transmittance in the near-infrared wavelength region while maintaining a wavelength dependence of the refractive index similar to that of JP2006-220689A.

The present inventors have conducted intensive studies to achieve the above-described object, and by improving the refractive index on the short wavelength side and adjusting the wavelength dependence of the refractive index, the present inventors have come up with the idea of reducing the amount of ITO particles added and increasing the transmittance in the near-infrared wavelength region. Based on this idea, the present invention is completed by further studies.

That is, specific methods for achieving the above-described object are as follows.

[1] A resin composition comprising:
an indium tin oxide particle; and
a near-ultraviolet light-absorbing organic compound,
in which the near-ultraviolet light-absorbing organic compound has a first wavelength of 340 nm to 400 nm, which first shows a maximum value in a case where an absorbance is measured from a wavelength of 800 nm, and
in a case where a maximum absorbance in a range of 340 nm to 400 nm is defined as $Abs(\lambda\ max)$, an absorbance at a wavelength of 410 nm is defined as $Abs(410\ nm)$, and an absorbance at a wavelength of 430 nm is defined as $Abs(430\ nm)$, both the following two expressions are satisfied, $(Abs(\lambda\ max) - Abs(410\ nm))/Abs(\lambda\ max) \geq 0.97$ $1.00 \geq (Abs(\lambda\ max) - Abs(410\ nm))/(Abs(\lambda\ max) - Abs(430\ nm)) \geq 0.97.$

[2] The resin composition according to [1],
in which the following P1 in the near-ultraviolet light-absorbing organic compound is 0.005 or more, $P1 = (Abs(\lambda\ max) - Abs(410\ nm))/(410 - \lambda\ max),$

[3] The resin composition according to [1] or [2],
in which the near-ultraviolet light-absorbing organic compound is a compound represented by General Formula 1.

$Pol_1\text{-}Sp_1\text{-}L_1\text{-}Ar\text{-}L_2\text{-}Sp_2\text{-}Pol_2$ (General Formula 1)

In the formula, Ar is any one of aromatic ring groups represented by General Formulae 2-1 to 2-4,

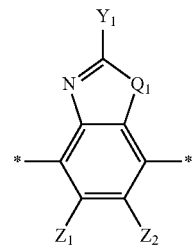

General Formula 2-1

-continued

General Formula 2-2

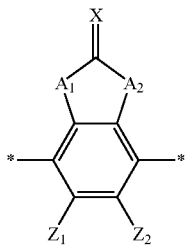

General Formula 2-3

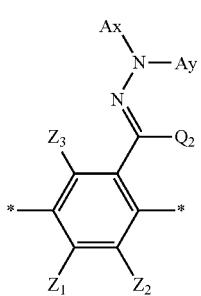

General Formula 2-4

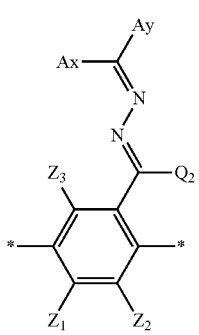

In the formulae, $Q_1$ represents —S—, —O—, or $NR_{11}$—, where $R_{11}$ represents a hydrogen atom or an alkyl group having 1 to 6 carbon atoms, $Y_1$ represents an alkyl group having 1 to 6 carbon atoms, which may have a substituent, an aromatic hydrocarbon group having 6 to 12 carbon atoms, which may have a substituent, or an aromatic heterocyclic group having 3 to 12 carbon atoms, which may have a substituent, $Z_1$, $Z_2$, and $Z_3$ each independently represent a hydrogen atom, an aliphatic hydrocarbon group having 1 to 20 carbon atoms, which may have a substituent, an alkoxy group having 1 to 20 carbon atoms, which may have a substituent, an alicyclic hydrocarbon group having 3 to 20 carbon atoms, which may have a substituent, a monovalent aromatic hydrocarbon group having 6 to 20 carbon atoms, which may have a substituent, a halogen atom, a cyano group, a nitro group, —$NR_{12}R_{13}$, or $SR_{12}$, where $Z_1$ and $Z_2$ may be bonded to each other to form an aromatic hydrocarbon ring which may have a substituent or an aromatic hetero ring which may have a substituent, and $R_{12}$ and $R_{13}$ each independently represent a hydrogen atom or an alkyl group having 1 to 6 carbon atoms, $A_1$ and $A_2$ each independently represent a group selected from the group consisting of —O—, $NR_{21}$-, —S—, and CO—, where $R_{21}$ represents a hydrogen atom or a substituent, X represents O, S, C to which a hydrogen atom or a substituent is bonded, or N to which a hydrogen atom or a substituent is bonded, Ax represents an organic group having 1 to 30 carbon atoms, which has at least one aromatic ring selected from the group consisting of an aromatic hydrocarbon ring and an aromatic hetero ring, Ay represents a hydrogen atom, an alkyl group having 1 to 6 carbon atoms, which may have a substituent, or an organic group having 1 to 30 carbon atoms, which has at least one aromatic ring selected from the group consisting of an aromatic hydrocarbon ring and an aromatic hetero ring, where the aromatic ring included in Ax and Ay may have a substituent, and Ax and Ay may be bonded to each other to form a ring which may have a substituent, and $Q_2$ represents a hydrogen atom or an alkyl group having 1 to 6 carbon atoms, which may have a substituent.

$L_1$ and $L_2$ each independently represent a single bond or a linking group selected from the group consisting of —O—, —S—, —C(=O)—, —OC(=O)—, —C(=O)O—, —OC(=O)O—, —$NR_{101}$C(=O)—, —C(=O)$NR_{102}$—, —OC(=O)$NR_{103}$—, —$NR_{104}$C(=O)O—, —SC(=O)—, and C(=O)S—, where $R_{101}$, $R_{102}$, $R_{103}$, and $R_{104}$ each independently represent -$Sp_3$-$Pol_3$ or a halogen atom, $Sp_1$ and $Sp_2$ each independently represent a single bond or a linking group selected from the group consisting of a linear alkylene group having 1 to 30 carbon atoms, which may have a substituent, and a group in which, in a linear alkylene group having 2 to 30 carbon atoms, which may have a substituent, one —$CH_2$— or two or more —$CH_2$—'s not adjacent to each other are replaced with —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S—, where $R_{201}$, $R_{202}$, $R_{203}$, and $R_{204}$ each independently represent -$Sp_4$-$Pol_4$ or a halogen atom, and $Sp_3$ and $Sp_4$ each independently represent a single bond or a divalent linking group, and $Pol_1$, $Pol_2$, $Pol_3$ and $Pol_4$ each independently represent a hydrogen atom or a polymerizable group, where the compound represented by General Formula 1 has at least one polymerizable group.

[4] The resin composition according to [3],
in which Ar is the aromatic ring group represented by General Formula 2-2.

[5] The resin composition according to [3] or [4],
in which both $L_1$ and $L_2$ are —O—, —OC(=O)—, —OC(=O)O—, or O—C(=O)NH—.

[6] The resin composition according to [5],
in which both $L_1$ and $L_2$ are —O—.

[7] The resin composition according to any one of [3] to [6],
in which all of the polymerizable groups are (meth)acryloyloxy groups.

[8] The resin composition according to any one of [3] to [7],
in which any of $Pol_1$ or $Pol_2$ is a (meth)acryloyloxy group.

[9] A cured product of the resin composition according to any one of [1] to [8],
in which a refractive index at a wavelength of 486.13 nm is 1.42 to 1.60, and
an Abbe number is 15 to 25.

[10] A diffractive optical element comprising:
the cured product according to [9],
in which the diffractive optical element includes a surface having a diffraction grating shape and formed of the cured product.

[11] A multilayer diffractive optical element comprising:
a first diffractive optical element; and
a second diffractive optical element,
in which the first diffractive optical element is the diffractive optical element according to [10], and
the surface of the first diffractive optical element, which has a diffraction grating shape, and a surface of the second diffractive optical element, which has a diffraction grating shape, face each other.

[12] The multilayer diffractive optical element according to [11],
in which a refractive index of the second diffractive optical element at a wavelength of 486.13 nm is 1.55 to 1.70, and is larger than a refractive index of the first diffractive optical element at the wavelength of 486 nm, and
an Abbe number of the second diffractive optical element is 35 to 60.

[13] The multilayer diffractive optical element according to [11] or [12],
in which the surface of the first diffractive optical element, which has a diffraction grating shape, and the surface of the second diffractive optical element, which has a diffraction grating shape, are in contact with each other.

[14] The multilayer diffractive optical element according to any one of [11] to [13], further comprising:
a transparent substrate,
in which the first diffractive optical element, the second diffractive optical element, and the transparent substrate are arranged in this order.

According to the present invention, a novel resin composition including ITO particles is provided, A cured product of the resin composition of the aspect of the present invention can be used as a material for producing a low Abbe number diffractive optical element in a multilayer diffractive optical element, can provide excellent diffraction efficiency, and has high light transmittance in the near-infrared wavelength region.

BRIEF DESCRIPTION OF THE DRAWINGS

FIG. 1 is a diagram showing absorption spectra of Example 6 (compound IV-15) and Comparative Example 3 (compound C-1).

DESCRIPTION OF THE PREFERRED EMBODIMENTS

Hereinafter, the present invention will be described in detail. The description of the constitutional requirements described below is made on the basis of representative embodiments and specific examples, but it should not be construed that the present invention is limited thereto. In the present specification, a numerical range represented by using "to" means a range including numerical values described before and after "to" as a lower limit value and an upper limit value.

In the present specification, "(meth)acrylate" represents either one of both acrylate and methacrylate, and "(meth)acryloyl" represents either one or both of acryloyl and methacryloyl. The monomer in the present invention is distinguished from an oligomer and a polymer, and refers to a compound having a weight-average molecular weight of 1,000 or less.

In the present specification, the term aliphatic hydrocarbon group refers to a group obtained by removing one optional hydrogen atom from a linear or branched alkane, a linear or branched alkene, or a linear or branched alkyne. In the present specification, the aliphatic hydrocarbon group is preferably an alkyl group obtained by removing one optional hydrogen atom from a linear or branched alkane.

In the present specification, the term alkyl group refers to a linear or branched alkyl group. Examples of the alkyl group include a methyl group, an ethyl group, a propyl group, an isopropyl group, a butyl group, an isobutyl group, a sec-butyl group, a tert-butyl group, a pentyl group, an 1-methylbutyl group, a 3-methylbutyl group, a hexyl group, an 1-methylpentyl group, a 4-methylpentyl group, a heptyl group, an 1-methylhexyl group, a 5-methylhexyl group, an octyl group, an 1-methylheptyl group, a nonyl group, an 1-methyloctyl group, a decyl group, an undecyl group, a dodecyl group, a tridecyl group, a tetradecyl group, a pentadecyl group, a hexadecyl group, a heptadecyl group, an octadecyl group, a nonadecil group, and an eicosyl group. The same applies to an alkyl group in a group (an alkoxy group, an alkoxycarbonyl group, an acyl group, and the like) including the alkyl group.

In addition, in the present specification, examples of a linear alkylene group include a group obtained by removing one hydrogen atom bonded to each terminal carbon from a linear alkyl group among the above-described alkyl groups.

In the present specification, examples of an alicyclic hydrocarbon ring include cyclopropane, cyclobutane, cyclopentane, cyclohexane, cycloheptane, cyclooctane, cyclononane, and cyclohexane.

In the present specification, examples of an unsaturated hydrocarbon ring include indene, indane, and fluorene.

In the present specification, the term alicyclic hydrocarbon group refers to a cycloalkyl group obtained by removing one optional hydrogen atom from a cycloalkane. Examples of the alicyclic hydrocarbon group include a cyclopropyl group, a cyclobutyl group, a cyclopentyl group, a cyclohexyl group, a cycloheptyl group, a cyclooctyl group, a cyclononyl group, and a cyclodecyl group, and a cycloalkyl group having 3 to 12 carbon atoms is preferable.

In the present specification, a cycloalkylene refers to a divalent group obtained by removing two optional hydrogen atoms from a cycloalkane. Examples of the cycloalkylene group include a cyclohexylene group.

In the present specification, the term aromatic ring refers to either one or both an aromatic hydrocarbon ring and an aromatic hetero ring.

In the present specification, examples of an aromatic hydrocarbon ring include benzene, biphenyl, biphenylene, naphthalene, anthracene, and phenanthrene.

In the present specification, the term aromatic hydrocarbon group refers to a monovalent group obtained by removing one optional hydrogen atom from the aromatic hydrocarbon ring, Examples thereof include a phenyl group, a biphenyl group, an 1-naphthyl groups, a 2-naphthyl groups, an 1-anthracenyl group, a 2-anthracenyl group, a 3-anthracenyl group, a 4-anthracenyl group, a 9-anthracenyl group, an 1-phenanthrenyl group, a 2-phenanthrenyl group, a 3-phenanthrenyl group, a 4-phenanthrenyl group, and a 9-phenanthrenyl group. In the present specification, the term divalent aromatic hydrocarbon group refers to a divalent group obtained by removing two optional hydrogen atoms from the aromatic hydrocarbon ring, and examples thereof include a divalent group obtained by removing one optional hydrogen atom from the above-described (monovalent) aromatic hydrocarbon group.

In the present specification, examples of the aromatic hetero ring include furan, thiophene, pyrrole, imidazole, isothiazole, isoxazole, pyridine, pyrazine, quinoline, benzofuran, benzothiazole, and benzoxazole.

In the present specification, the term aromatic heterocyclic group refers to a monovalent group obtained by removing one optional hydrogen atom from the aromatic hetero ring. Examples of the monovalent aromatic heterocyclic group include a furyl group, a thienyl group (preferably, a 2-thienyl group), a pyrrolyl group, an imidazolyl group, an isothiazolyl group, an isooxazolyl group, a pyridyl group, a pyrazinyl group, a quinolyl group, a benzofuranyl group (preferably a 2-benzofuranyl group), a benzothiazolyl group (preferably, a 2-benzothiazolyl group), and a benzoxazolyl group (preferably, a 2-benzoxazolyl group). In the present specification, the term divalent aromatic heterocyclic group refers to a divalent group obtained by removing two optional hydrogen atoms from the aromatic hetero ring, and examples thereof include a divalent group obtained by removing one optional hydrogen atom from the above-described (monovalent) aromatic heterocyclic group.

«Resin Composition»

The resin composition according to an embodiment of the present invention includes indium tin oxide particles and a near-ultraviolet light-absorbing organic compound. The resin composition according to the embodiment of the present invention may include other components in addition to these components. Hereinafter, each component will be described.

<Near-Ultraviolet Light-Absorbing Organic Compound>

The resin composition according to the embodiment of the present invention includes near-ultraviolet light-absorbing organic compound which exhibits light absorption in a near-ultraviolet wavelength region. The above-described light absorption of the near-ultraviolet light-absorbing organic compound does not extend to a visible light region, and the near-ultraviolet light-absorbing organic compound exhibits substantially no light absorption at a wavelength of 130 to 800 nm. By adding such a near-ultraviolet light-absorbing organic compound to a resin composition including indium tin oxide particles, even in a case where the amount of indium tin oxide particles added is small, it is possible to obtain a chromatic aberration reducing effect in a wide wavelength range in a case where the resin composition is used as a material having a low refractive index and a low Abbe number in a multilayer diffractive optical element. Since the amount of indium tin oxide particles added can be reduced, it is possible to suppress a decrease in transmittance in the near-infrared wavelength region.

Specifically, the near-ultraviolet light-absorbing organic compound has a first wavelength of 340 nm to 400 nm, which first shows a maximum value in a case where an absorbance is measured from a wavelength of 800 nm. That is, the absorption spectrum in a wavelength range of 340 nm to 800 nm has an absorbance peak having a maximum value only in a range of 340 nm to 400 nm. The maximum value in the range of 340 nm to 400 nm may be one or two or more. The wavelength which first shows the maximum value in a case where an absorbance is measured from a wavelength of 800 nm is preferably 340 nm to 385 nm and more preferably 350 nm to 380 nm. In addition, the maximum value exhibiting the highest absorbance among maximum values in the range of 340 nm to 400 nm is preferably 340 nm to 385 nm and more preferably 350 nm to 380 nm. Here, it is sufficient that the absorption spectrum is measured with a solution of the near-ultraviolet light-absorbing organic compound, and it is assumed that the absorption spectrum is obtained by placing a solvent-only cell in a sample optical path and a control optical path to adjust the absorbance to zero, and then replacing the sample optical path-side cell with a solution of the near-ultraviolet light-absorbing organic compound for measurement.

In addition, in a case where the highest maximum value (absorbance at a wavelength with the highest absorbance among the maximum values in the range of 340 nm to 400 nm) among the above-described maximum values in the range of 340 nm to 400 nm is defined as Abs($\lambda$ max), an absorbance of the above-described absorption spectrum at a wavelength of 410 nm is defined as Abs(410 nm), and an absorbance of the above-described absorption spectrum at a wavelength of 430 nm is defined as Abs(430 nm), it is sufficient that the near-ultraviolet light-absorbing organic compound satisfies the following expressions.

$$(Abs(\lambda\ max)-Abs(410\ nm))/Abs(\lambda\ max) \geq 0.97$$

$$1.00 \geq (Abs(\lambda\ max)-Abs(410\ nm))/(Abs(\lambda\ max)-Abs(430\ nm)) \geq 0.97$$

Preferably, it is sufficient that the following expressions are satisfied.

$$(Abs(\lambda\ max)-Abs(410\ nm))/Abs(\lambda\ max) \geq 0.98$$

$$1.00 \geq (Abs(\lambda\ max)-Abs(410\ nm))/(Abs(\lambda\ max)-Abs(430\ nm)) \geq 0.98$$

That is, both Abs(410 nm) and Abs(430 nm) are small values with respect to Abs($\lambda$ max), and are substantially close to 0.

The measurement conditions of the absorption spectra are not particularly limited. As an example, using a 20 mg/L solution of the near-ultraviolet light-absorbing organic compound, the absorption spectrum can be measured using UV-2550 manufactured by Shiniadzu Corporation. In this condition, it is preferable that the following expression is satisfied.

$$(Abs(\lambda\ max)-Abs(410\ nm))/(410-\lambda\ max) \geq 0.005$$

The solvent used for measuring the absorption spectrum is not particularly limited as long as the solvent can dissolve the near-ultraviolet light-absorbing organic compound, and for example, tetrahydrothran can be used.

The near-ultraviolet light-absorbing organic compound included in the resin composition according to the embodiment of the present invention is preferably a polymerizable compound. That is, the near-ultraviolet light-absorbing organic compound is preferably a compound having a polymerizable group. Examples of the polymerizable group include polymerizable groups represented by Formulae Pol-1 to Pol-6.

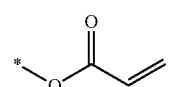

Pol-1

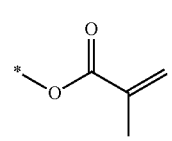

Pol-2

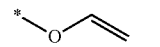

Pol-3

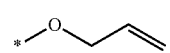

Pol-4

Pol-5

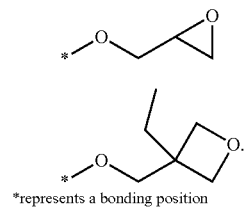

Pol-6

*represents a bonding position

Among these, a (meth)acryloyloxy group (Pol-1 and Pol-2) is preferable. The near-ultraviolet light-absorbing organic compound may have 1 or more polymerizable groups, and preferably has 1 to 4 polymerizable groups and more preferably has 1 or 2 polymerizable groups.

The near-ultraviolet light-absorbing organic compound included in the resin composition according to the embodiment of the present invention is also preferably a compound including an aromatic ring as a partial structure.

Compound Represented by General Formula 1

The near-ultraviolet light-absorbing organic compound included in the resin composition according to the embodiment of the present invention is preferably a compound represented by General Formula 1. The compound represented by General Formula 1 includes a benzene ring with a fused ring of benzene and a hetero ring, such as benzodithiol and benzothiazole, or a hydrazone as a substituent in its structure. The present inventors have found that the compound represented by General Formula 1 has the above-described spectral characteristics, and a cured product formed from the resin composition containing the compound represented by General Formula 1 has a low Abbe number (vD). Further, the present inventors have found that the cured product formed from the resin composition containing the compound represented by General Formula 1 has a high heat shock resistance. In the present specification, the heat shock resistance refers to an ability to relieve stress in a case of thermal change of the cured product.

$Pol_1-Sp_1-L_1-Ar-L_2-Sp_2-Pol_2$ (General Formula 1)

In the formula, Ar is any one of aromatic ring groups represented by General Formulae 2-1 to 2-4.

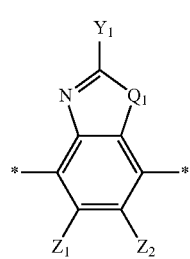

General Formula 2-1

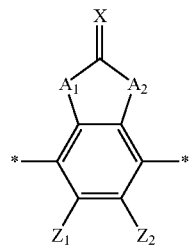

General Formula 2-2

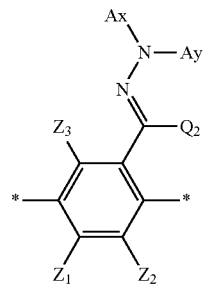

General Formula 2-3

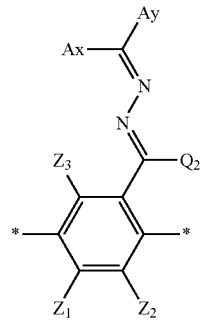

General Formula 2-4

In General Formulae 2-1 to 2-4, $Q_1$ represents —S—, —O—, or $NR_{11}$—, where $R_{11}$ represents a hydrogen atom or an alkyl group having 1 to 6 carbon atoms, $Y_1$ represents an alkyl group having 1 to 6 carbon atoms, which may have a substituent, an aromatic hydrocarbon group having 6 to 12 carbon atoms, which may have a substituent, or an aromatic heterocyclic group having 3 to 12 carbon atoms, which may have a substituent, $Z_1$, $Z_2$, and $Z_3$ each independently represent a hydrogen atom, an aliphatic hydrocarbon group having 1 to 20 carbon atoms, which may have a substituent, an alkoxy group having 1 to 20 carbon atoms, which may have a substituent, an alicyclic hydrocarbon group having 3 to 20 carbon atoms, which may have a substituent, a monovalent aromatic hydrocarbon group having 6 to 20 carbon atoms, which may have a substituent, a halogen atom, a cyano group, a nitro group, —$NR_{12}R_{13}$, or $SR_{12}$, where $Z_1$ and $Z_2$ may be bonded to each other to form an aromatic hydrocarbon ring which may have a substituent or an aromatic hetero ring which may have a substituent, and $R_{12}$ and $R_{13}$ each independently represent a hydrogen atom or an alkyl group having 1 to 6 carbon atoms, $A_1$ and $A_2$ each independently represent a group selected from the group consisting of —O—, —$NR_{21}$— ($R_{21}$ represents a hydrogen atom or a substituent), —S—, and —C(=O)—, X represents O, S, C to which a hydrogen atom or a substituent is bonded, or N to which a hydrogen atom or a substituent is bonded, Ax represents an organic group having 1 to 30 carbon atoms, which has at least one aromatic ring selected from the group consisting of an aromatic hydrocarbon ring and an aromatic hetero ring, Ay represents a hydrogen atom, an alkyl group having 1 to 6 carbon atoms, which may have a substituent, or an organic group having 1 to 30 carbon atoms, which has at least one aromatic ring selected from the group consisting of an aromatic hydrocarbon ring and an aromatic hetero ring, where the aromatic ring included in Ax and Ay may have a substituent, and Ax and Ay may be bonded to each other to form a ring which may have a substituent, and Q$_2$ represents a hydrogen atom or an alkyl group having 1 to 6 carbon atoms, which may have a substituent.

* represents a bonding site with L$_1$ or L$_2$.

With regard to the definition and preferred range of each substituent in General Formulae 2-1 to 2-4, the descriptions regarding Y$^1$, Q$^1$, and Q$^2$ in the compound (A) described in JP2012-21068A can be referred to for Y$_1$, Z$_1$, and Z$_2$, the descriptions regarding A$_1$, A$_2$, and X in the compound represented by General Formula (I) described in JP2008-107767A can be referred to for A$_1$, A$_2$, and X, the descriptions regarding A$^x$, A$^y$, and Q$^1$ in the compound represented by General Formula (I) described in WO2013/018526A can be referred for Ax, Ay, and Q$_2$ in General Formula 2-3, and the descriptions regarding A$^a$, A$^b$, and Q$^{11}$ in the compound represented by General Formula (II) described in WO2013/018526A can be referred for Ax, Ay, and Q$_2$ in General Formula 2-4. The description regarding Q$^1$ in the compound (A) described in JP2012-21068A can be referred to for Z$_3$.

X in General Formula 2-2 is preferably C to which two substituents are bonded, and both A$_1$ and A$_2$ are preferably —S—. In General Formula 2-3, as the ring in a case where Ax and Ay are bonded to each other to form a ring which may have a substituent, an alicyclic hydrocarbon ring, an aromatic hydrocarbon ring, or an aromatic hetero ring is preferable, and an aromatic hetero ring is more preferable. In General Formula 2-4, as the ring in a case where Ax and Ay are bonded to each other to form a ring which may have a substituent, an unsaturated hydrocarbon ring is preferable.

Ar in General Formula 1 is preferably the aromatic ring group represented by General Formula 2-2.

As the aromatic ring group represented by General Formula 2-2, an aromatic ring group represented by General Formula 2-2-1 is particularly preferable.

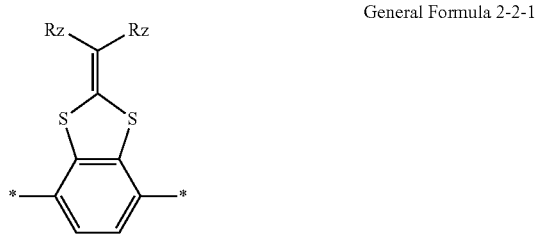

General Formula 2-2-1

In the formula, Rz represents a substituent. Examples of the substituent represented by Rz include a substituent exemplified as a substituent of Sp$_1$ described later. Two Rz's may be the same or different from each other. In addition, the two Rz's may be bonded to each other to form a ring. As the ring formed in this case, a 5-membered ring or a 6-membered ring is preferable, a 5-membered ring or 6-membered ring including nitrogen or oxygen as an element constituting the ring is more preferable. In particular, it is preferable to be a ring represented by any one of the following formulae.

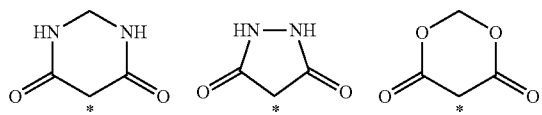

In the above formulae, * represents a position of a carbon atom where the two Rz's are bonded in General Formula 2-2-1, respectively. In addition, the ring represented by the above formulae may have a substituent in nitrogen or carbon. As the substituent in this case, an alkyl group having 1 to 6 carbon atoms is preferable, and a linear alkyl group having 1 to 4 carbon atoms is more preferable.

As the aromatic ring group represented by General Formula 2-2-1, an aromatic ring group in which at least one of Rz's is a cyano group or an aromatic ring group in which two Rz's are bonded to each other to form a ring is preferable, and an aromatic ring group in which both Rz's are cyano groups is more preferable.

In General Formula 1, L$_1$ and L$_2$ each independently represent a single bond or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)O—, —SC(=O)—, and C(=O)S—. In the above description of the linking group, it is assumed that the left side is bonded to Ar and the right side is bonded to Sp$_1$ or Sp$_2$. R$_{101}$, R$_{102}$, R$_{103}$, and R$_{104}$ each independently represent -Sp$_3$-Pol$_3$ or a halogen atom. L$_1$ and L$_2$ are each independently preferably —O—, —OC(=O)—, —C(=O)O—, —OC(=O)O—, —NR$_{101}$C(=O)—, —C(=O)NR$_{102}$—, —OC(=O)NR$_{103}$—, or —NR$_{104}$C(=O)O—, more preferably —O—, —OC(=O)—, —OC(=O)O—, or —OC(=O)NR$_{103}$—, and still more preferably —O—, R$_{101}$, R$_{102}$, R$_{103}$, and R$_{104}$ are each independently preferably a hydrogen atom, an alkyl group having 1 to 4 carbon atoms, or a halogen atom.

L$_1$ and L$_2$ may be the same or different from each other, but it is preferable that L$_1$ and L$_2$ are the same.

Sp$_3$'s in R$_{101}$, R$_{102}$, R$_{103}$, and R$_{104}$ each independently represent a single bond or a divalent linking group. Examples of the divalent linking group include the following linking groups and linking groups selected from the group consisting of two or more combinations of the following linking groups:

a linear alkylene group which may have a substituent; a cycloalkylene group (for example, a trans-1,4-cyclohexylene group) which may have a substituent; a divalent aromatic hydrocarbon group (for example, an 1,4-phenylene group) which may have a substituent; a divalent aromatic heterocyclic group which may have a substituent; —O—; —S—; —C(=O)—; —OC(=O)—; —C(=O)O—; —OC(=O)O—; —NR$_{201}$C(=O)—; —C(=O)NR$_{202}$—; —OC(=O)NR$_{203}$—; —NR$_{204}$C(=O)O—; —SC(=O)—; and —C(=O)S—.

Examples of Sp$_3$ which is a divalent linking group include a linear alkylene group which may have a substituent; a cycloalkylene group which may have a substituent; a divalent aromatic hydrocarbon group which may have a substituent; a divalent aromatic heterocyclic group which may have a substituent; and a linking group in which two or more linking groups selected from the group consisting of a linear alkylene group which may have a substituent, a cycloalkylene group which may have a substituent, a divalent aromatic hydrocarbon group which may have a substituent, and a divalent aromatic heterocyclic group which may have a substituent are bonded to each other through a linking group selected from the group consisting of a single bond, —O—, —C(=O)—, —OC(=O)—, —C(=O)O—, —OC(=O)O—, —NR$_{201}$C(=O)—, and —C(=O)NR$_{202}$—, As the divalent linking group represented by Sp$_3$, a single bond or a linear alkylene group having 1 to 10 carbon atoms, which may have a substituent, is preferable, a linear alkylene group having 1 to 5 carbon atoms, which may have a substituent, is more preferable, a linear alkylene group having 1 to 3 carbon atoms, which may have a substituent, is still more preferable, and an unsubstituted linear alkylene group is particularly preferable.

$Pol_3$ in $R_{101}$, $R_{102}$, $R_{103}$, and $R_{104}$ has the same meaning as $Pol_1$ described later.

-$Sp_3$-$Pol_3$ is preferably a hydrogen atom or an alkyl group having 1 to 4 carbon atoms, which may have a substituent, and more preferably a hydrogen atom or an alkyl group having 1 to 4 carbon atoms.

In General Formula 1, $Sp_1$ and $Sp_2$ each independently represent a single bond or a linking group selected from the group consisting of a linear alkylene group having 1 to 30 carbon atoms, which may have a substituent, and a group in which, in a linear alkylene group having 2 to 30 carbon atoms, which may have a substituent, one —$CH_2$— or two or more —$CH_2$—'s not adjacent to each other are replaced with —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S—. Here, $R_{201}$, $R_{202}$, $R_{203}$, and $R_{204}$ each independently represent -$Sp_4$-$Pol_4$ or a halogen atom. $Sp_4$ and $Pol_4$ respectively have the same meanings as $Sp_3$ and $Pol_3$ described above, and the preferred ranges are also the same. $R_{201}$, $R_{202}$, $R_{203}$, and $R_{204}$ are each independently preferably a hydrogen atom, an alkyl group having 1 to 4 carbon atoms, or a halogen atom.

$Sp_1$ and $Sp_2$ may be the same or different from each other, but it is preferable that $Sp_1$ and $Sp_2$ are the same.

In $Sp_1$ and $Sp_2$ which are a group in which, in a linear alkylene group having 2 to 30 carbon atoms, —$CH_2$— is replaced with other divalent group selected from the group consisting of —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, —C(=O)S— described above, it is preferable that the other substituted divalent group is not directly bonded to $L_1$ or $L_2$. That is, it is preferable that the moiety substituted with the other divalent group described above is not the $L_1$-side terminal of $Sp_1$ and the $L_2$-side terminal of $Sp_2$.

The divalent linking group represented by $Sp_1$ and $Sp_2$ are each independently more preferably a linear alkylene group having 1 to 20 carbon atoms, which may have a substituent, or a group in which, in a linear alkylene group having 2 to 20 carbon atoms, which may have a substituent, one —$CH_2$— or two or more —$CH_2$—'s not adjacent to each other are replaced with —O—, —C(=O)—, —OC(=O)—, —C(=O)O—, —OC(=O)O—, —$NR_{201}$C(=O)—, —C(=O)$NR_{202}$—, —OC(=O)$NR_{203}$—, or —$NR_{204}$C(=O)O—, still more preferably a linear alkylene group having 1 to 10 carbon atoms, which may have a substituent, or a group in which, in a linear alkylene group having 2 to 10 carbon atoms, which may have a substituent, one —$CH_2$— or two or more —$CH_2$—'s not adjacent to each other are replaced with —O—, —C(=O)—, —OC(=O)—, or —C(=O)O—, and particularly preferably a linear alkylene group having 1 to 10 carbon atoms, which has no substituent or has a methyl group as a substituent, or a group in which, in a linear alkylene group having 2 to 10 carbon atoms, which has no substituent or has a methyl group as a substituent, one —$CH_2$— or two or more —$CH_2$—'s not adjacent to each other are replaced with —O—, —C(=O)—, —OC(=O)—, or —C(=O)O—.

In the above description of the linking group, it is assumed that the left side is bonded to $L_1$, $L_2$, or N (in a case of $Sp_3$) and the right side is bonded to $Pol_1$, $Pol_2$, or $Pol_3$.

With regard to the substituents in $Sp_1$, $Sp_2$, $Sp_3$, and General Formulae 2-1 to 2-4, the substituent in a case of being referred to "may have a substituent" is not particularly limited, and examples thereof include an alkyl group, a cycloalkyl group, an alkoxy group, an acyl group, an acyloxy group, an alkoxycarbonyl group, an amide group, an amino group, a halogen atom, a nitro group, a cyano group, and a substituent selected from the group consisting of groups composed of a combination of two or more of the above substituents. The substituent may be a group represented by -$Sp_5$-$Pol_5$. $Sp_5$ and $Pol_5$ respectively have the same meanings as $Sp_1$ and $Pol_1$, and the preferred ranges are also the same. The number of substituents is not particularly limited, and may be 1 to 4. In a case of having two or more substituents, the two or more substituents may be the same or different from each other.

In General Formula 1, $Pol_1$ and $Pol_2$ each independently represent a hydrogen atom or a polymerizable group. Examples of the polymerizable group include polymerizable groups represented by Formulae Pol-1 to Pol-6.

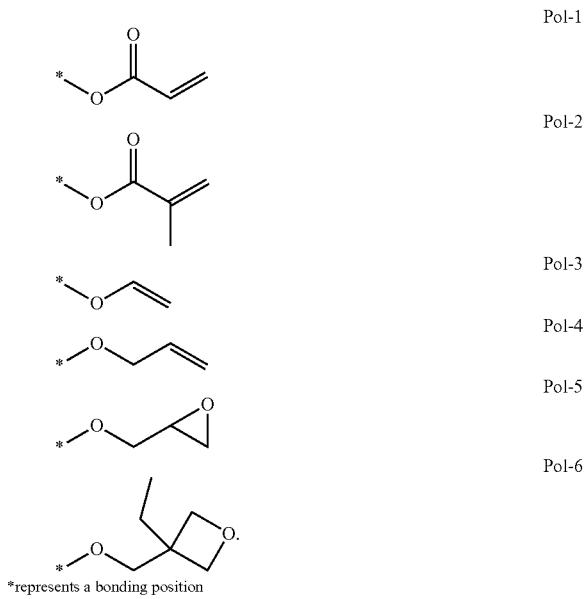

*represents a bonding position

Among these, a (meth)acryloyloxy group (Pol-1 and Pol-2) is preferable.

It is preferable that any one of the polymerizable group $Pol_1$ or $Pol_2$ is a (meth)acryloyloxy group, and it is more preferable that both the polymerizable groups $Pol_1$ and $Pol_2$ are (meth)acryloyloxy groups.

$Pol_1$ and $Pol_2$ may be the same or different from each other, but it is preferable that $Pol_1$ and $Pol_2$ are the same.

The compound represented by General Formula 1 has at least one polymerizable group. The compound represented by General Formula 1 preferably has at least two polymerizable groups.

Examples of a specific structure of $Pol_1$-$SP_1$-$L_1$- or $Pol_2$-$Sp_2$-$L_2$- include the following structures.

$Pol_1$-$SP_1$-$L_1$- and $Pol_2$-$Sp_2$-$L_2$- may be the same or different from each other, but it is preferable that $Pol_1$-$SP_1$-$L_1$- and $Pol_2$-$Sp_2$-$L_2$- are the same.

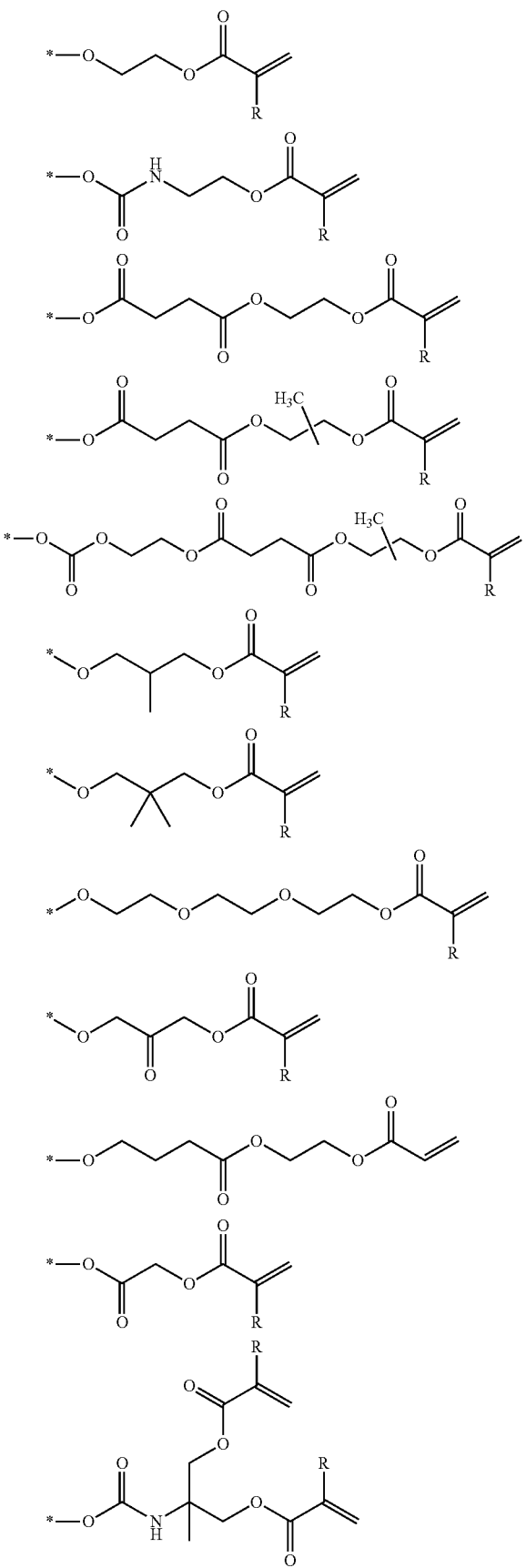
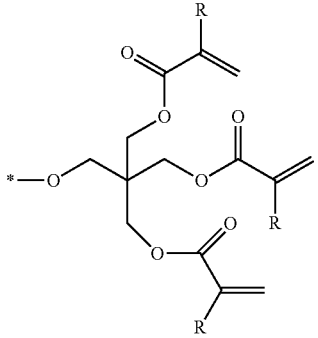

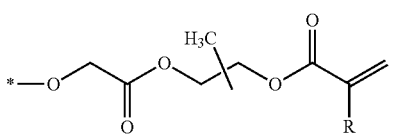

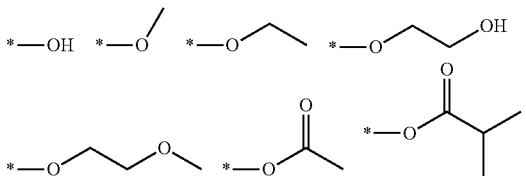

(R is a hydrogen atom or a methyl group, and * represents a bonding position to Ar)

In the present specification, the following structure indicates that two partial structures in which a methyl group is bonded to any one of carbons of an ethylene group are mixed.

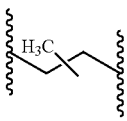

As described above, in the compound represented by General Formula 1, in a case where a linear alkylene group has a structure in which a substituent is substituted, structural isomers having different substitution positions of the substituent may exist. The compound represented by General Formula 1 may be a mixture of such structural isomers.

The compound represented by General Formula 1 is preferably a non-liquid crystalline compound.

Hereinafter, specific examples of the compound represented by General Formula 1, which is preferably used in the resin composition according to the embodiment of the present invention, will be shown, but the present invention is not limited to the following compounds. In the following structural formulae, Me represents a methyl group, Et represents an ethyl group, nPr represents an n-propyl group, iPr represents an isopropyl group, nBu represents an n-butyl group, and tBu represents a t-butyl group.

-continued
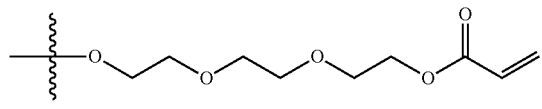 (I-19)
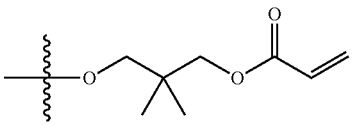 (I-20)
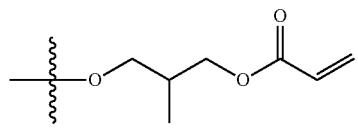 (I-21)
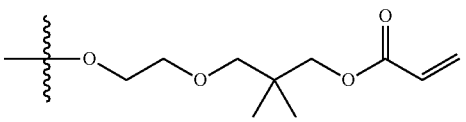 (I-22)
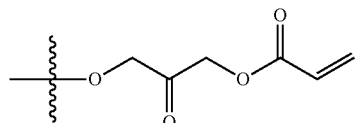 (I-23)
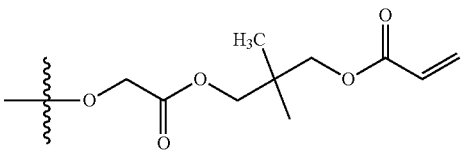 (I-24)
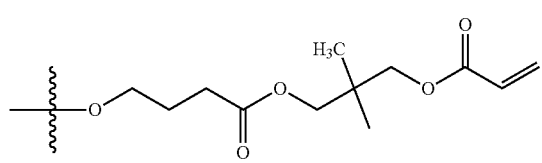 (I-25)
R =
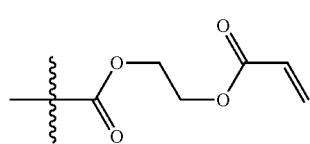 (III-1)
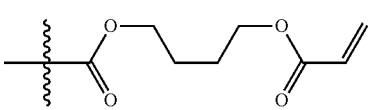 (III-2)
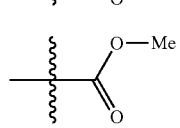 (III-3)
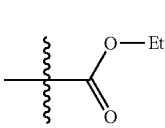 (III-4)
R =
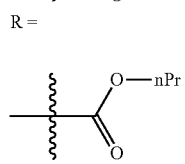 (III-5)
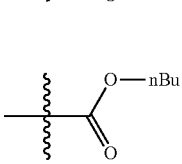 (III-6)
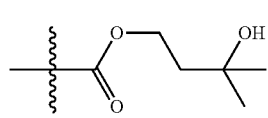 (III-7)
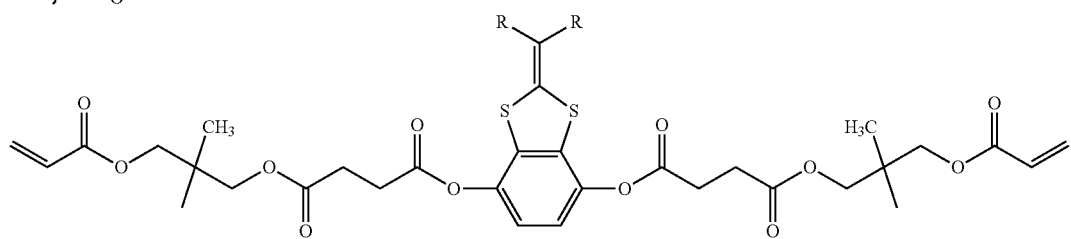

-continued
R =
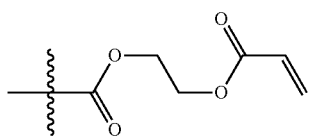
(III-8)
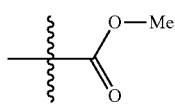
(III-10)
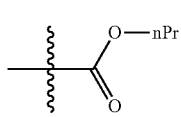
(III-12)
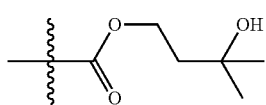
R =
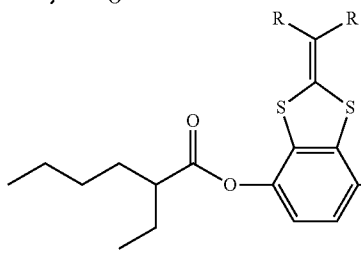
R =
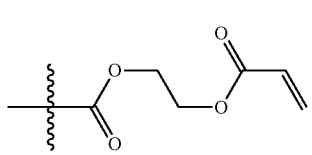
(III-15)
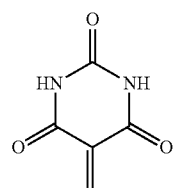
(III-9)
O—Et
(III-11)
O—nBu
(III-13)
(III-14)
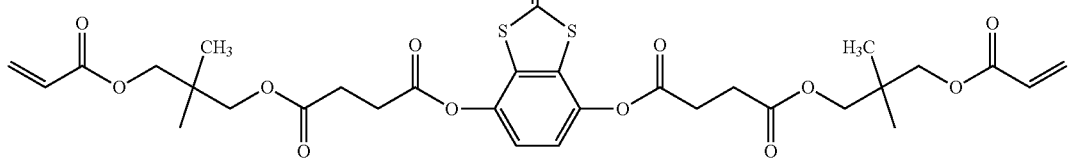
(III-16)
(III-17)
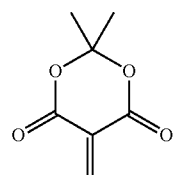
(III-18)
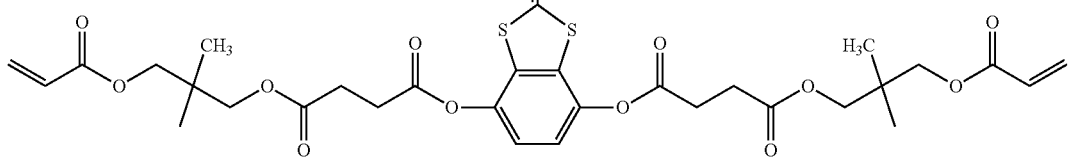

-continued
(III-19)
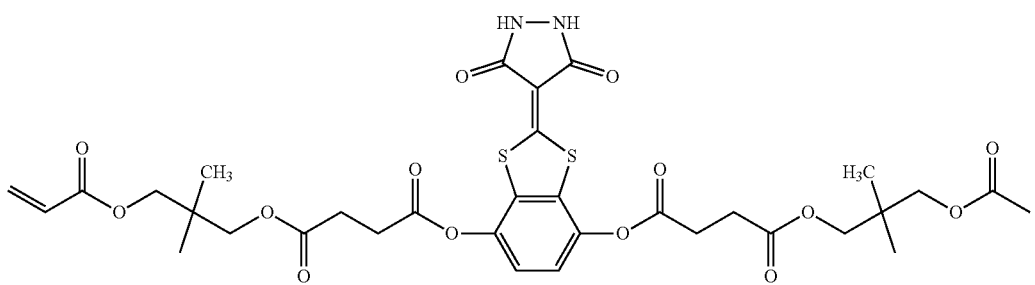
(III-20)
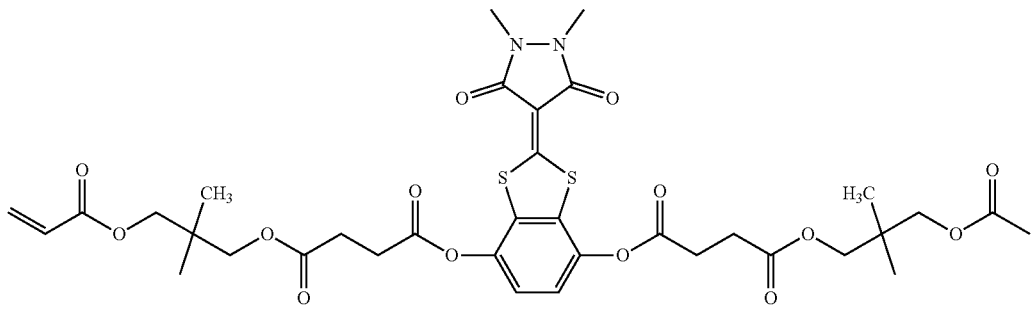
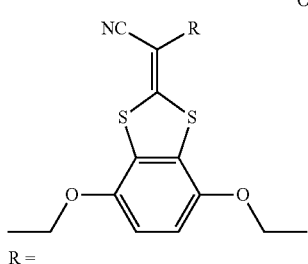
R =
(III-21)
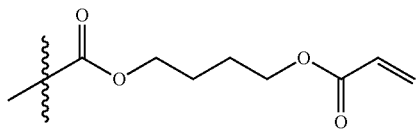
R =
(III-22)
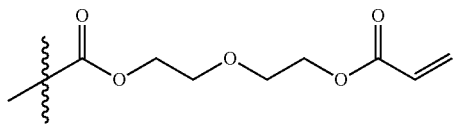
R =
(III-23)
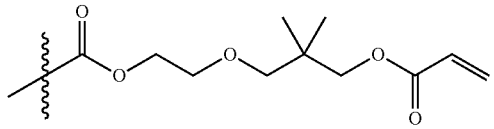
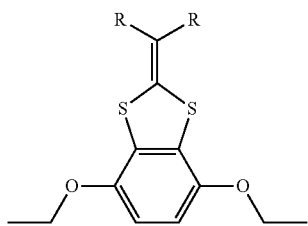

-continued
R =
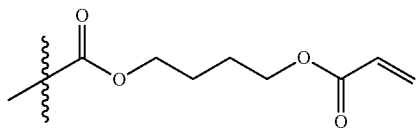
(III-24)
R =
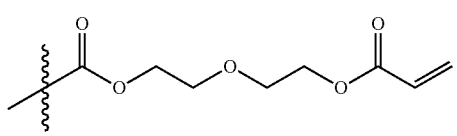
(III-25)
R =
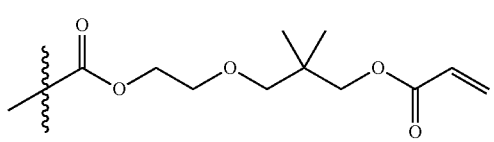
(III-26)
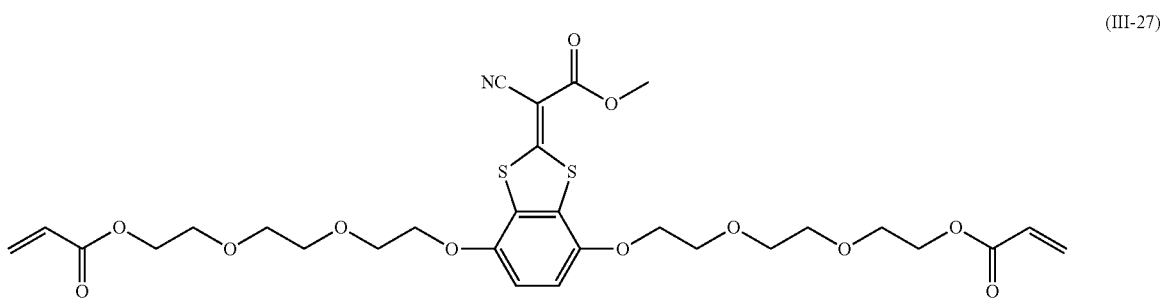
(III-27)
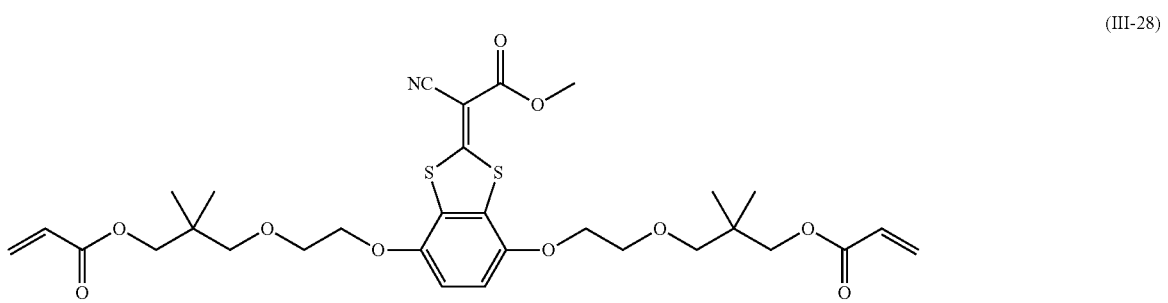
(III-28)
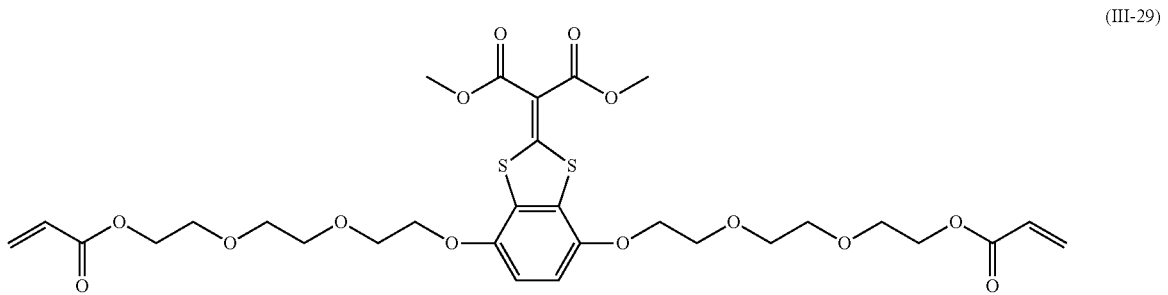
(III-29)

-continued
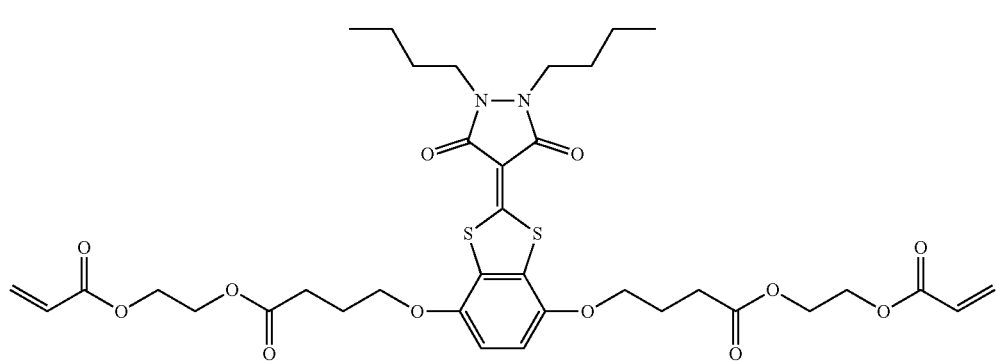
(III-30)
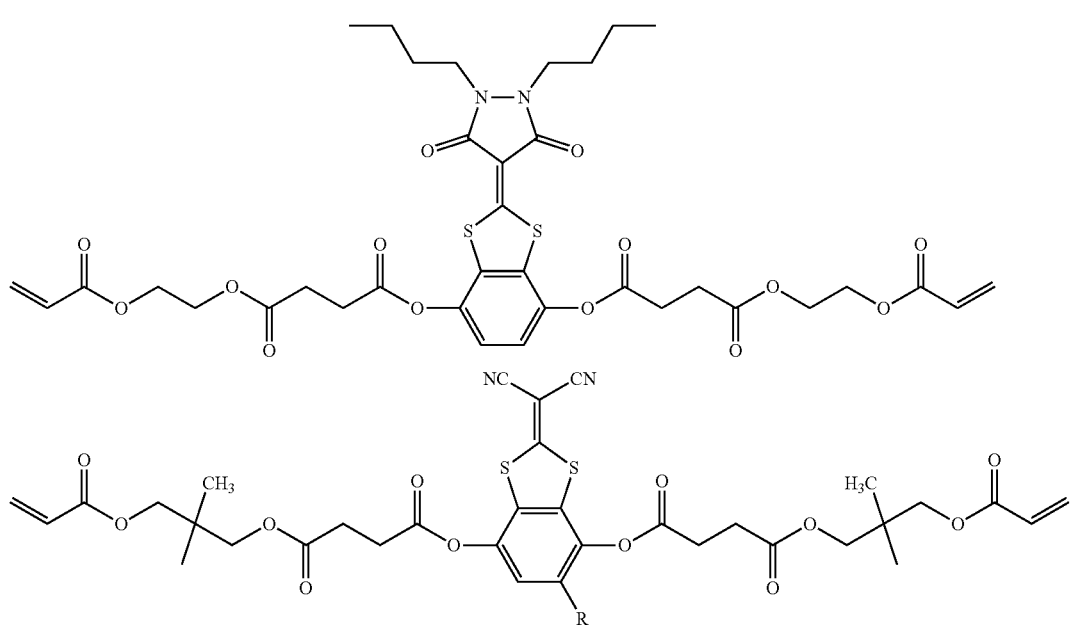
(III-31)
R =
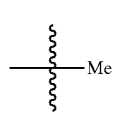 (IV-1)    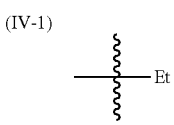 (IV-2)
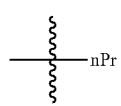 (IV-3)    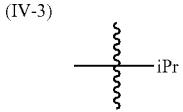 (IV-4)
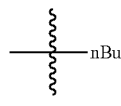 (IV-5)    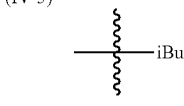 (IV-6)
R =
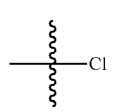 (IV-7)    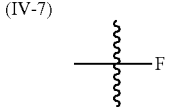 (IV-8)
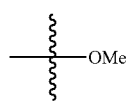 (IV-9)   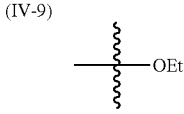 (IV-10)

(IV-11)
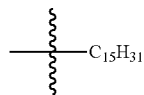
(IV-12)
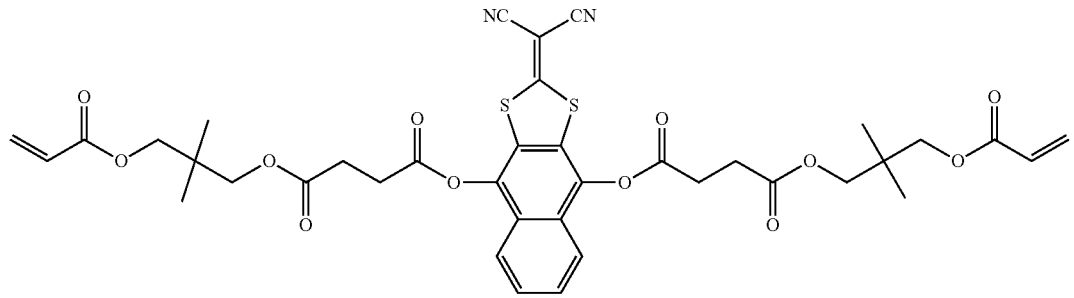
(IV-13)
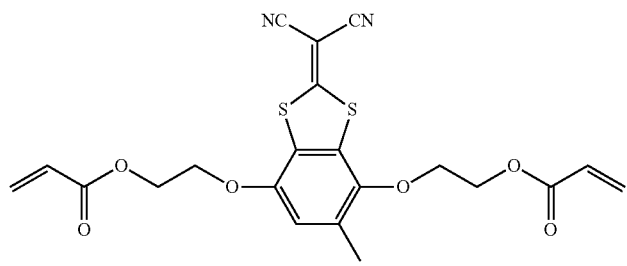
(IV-14)
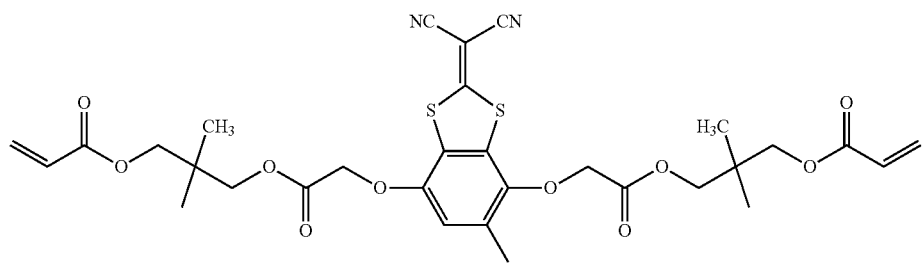
(IV-15)
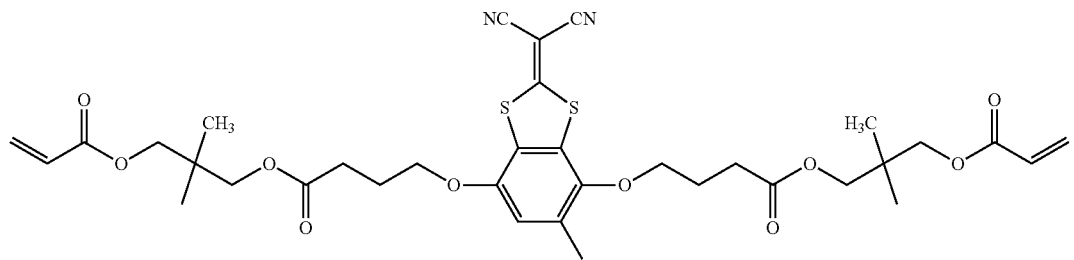
(IV-16)
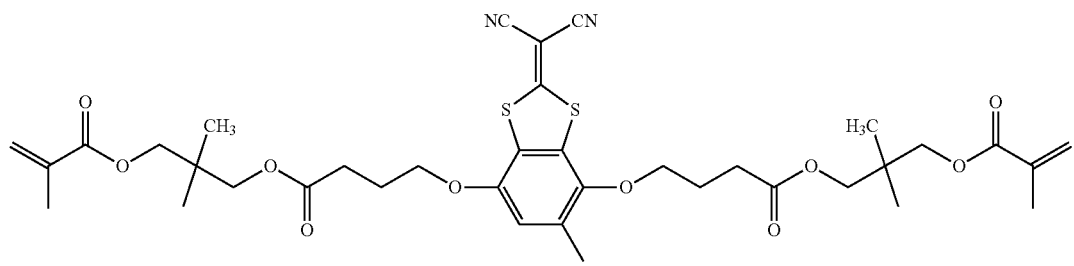

-continued
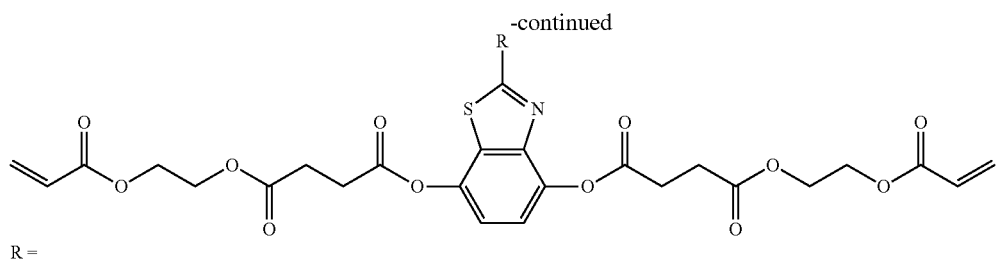
R =
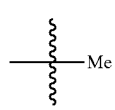
(V-1)
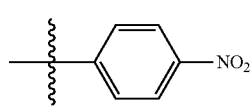
(V-2)
R =
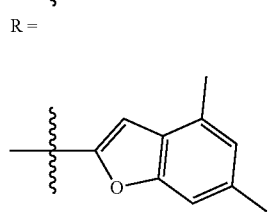
(V-3)
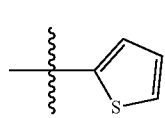
(V-4)
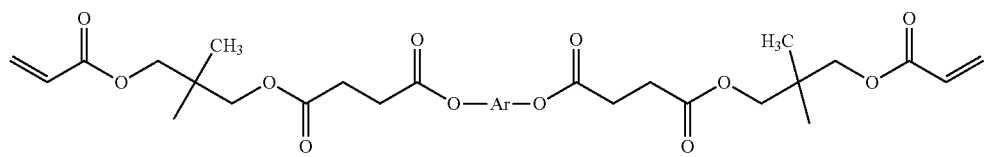
Ar =
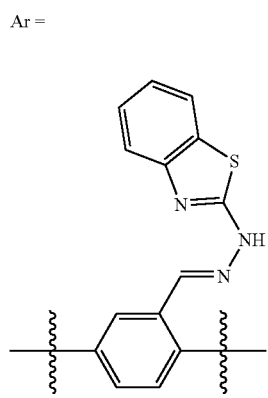
(VI-1)
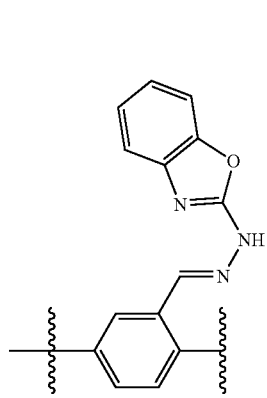
(VI-2)
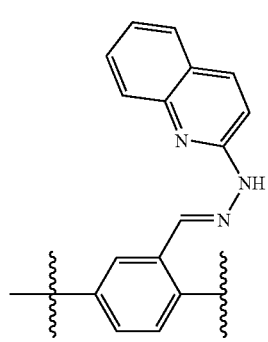
(VI-3)
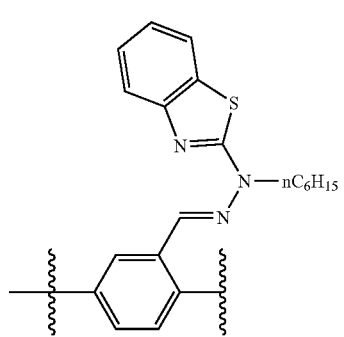
(VI-4)
Ar =

(VI-6) 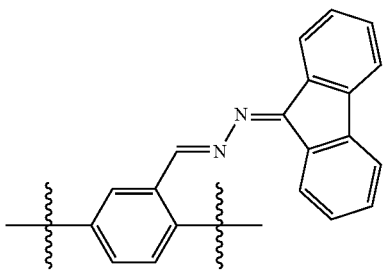

(VI-7) 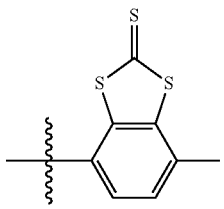

The compound represented by General Formula 1 may have one or two or more asymmetric carbons, and for such stereochemistry of asymmetric carbons, either the (R)-form or the (S)-form can be independently taken. In addition, the compound represented by General Formula 1 may be a mixture of optical isomers or steric isomers such as diastereoisomers. That is, the compound represented by General Formula 1 may be any kind of stereoisomer, any mixture of stereoisomers, or racemic isomer.

[Content and the Like of Near-Ultraviolet Light-Absorbing Organic Compound]

It is sufficient that the content of the near-ultraviolet light-absorbing organic compound in the resin composition is adjusted according to the above-described ABS($\lambda$ max) value of the near-ultraviolet light-absorbing organic compound and whether or not the near-ultraviolet light-absorbing organic compound is a polymerizable compound. Typically, with respect to the total mass (in a case of including a solvent, a mass of solid content excluding the solvent) of the resin composition, the content thereof is preferably 1% to 60% by mass, more preferably 5% to 50% by mass, still more preferably 10% by mass to 40% by mass, and particularly preferably 15% to 35% by mass. In a case where the content of the near-ultraviolet light-absorbing organic compound is within the above-described range, an effect of increasing the refractive index in the near-ultraviolet light region can be sufficiently obtained.

Two or more kinds of near-ultraviolet light-absorbing organic compounds may be contained in the resin composition. In a case of containing two or more kinds of near-ultraviolet light-absorbing organic compounds, the total content is preferably within the above-described range.

<Indium Tin Oxide Particles>

The resin composition according to the embodiment of the present invention includes indium tin oxide (ITO) particles. By adding ITO particles to the resin composition, it is possible to obtain a cured product having a lower refractive index as the wavelength in the visible light region is longer.

The particle size of ITO particles is preferably 5 nm to 50 nm. By setting the particle size to 50 nm or less, it is possible to prevent deterioration of transmittance due to Rayleigh scattering. In addition, by setting the particle size to 5 nm or more, it is possible to perform a production without technical difficulty. The particle size of the ITO particles can be obtained by averaging particle sizes which are measured by a transmission electron microscopy (TEM). That is, a minor axis and a major axis of one particle in an electron micrograph photographed by TEM are measured, and the average value thereof is determined as a particle size of one particle. In the present specification, particle sizes of 50 or more particles are averaged to obtain an average primary particle size.

It is preferable that the ITO particles are mixed, in a state of being dispersed in a solvent, with the above-described bifunctional or more (meth)acrylate compound and the acidic polymer described later to form the resin composition according to the embodiment of the present invention. After mixing, the solvent may or may not be removed by distillation or the like, but it is preferable to be removed.

The dispersibility of the ITO particles in a solvent can be improved by using surface-modified ITO particles. The surface modification of ITO particles is preferably performed with, for example, a monocarboxylic acid having 6 to 20 carbon atoms. It is preferable that the surface modification of ITO particles with a monocarboxylic acid is performed by covalently bonding a carboxyl group derived from the monocarboxylic acid to the ITO particle through an oxygen atom on the surface of the ITO particle, thereby forming an ester bond. Examples of the monocarboxylic acid having 6 to 20 carbon atoms include oleic acid (having 18 carbon atoms), stearic acid (having 18 carbon atoms), palmitic acid (having 16 carbon atoms), myristic acid (having 14 carbon atoms), and decanoic acid (having 10 carbon atoms), and oleic acid (having 18 carbon atoms) is preferable.

In the resin composition, a moiety (for example, a group derived from a monocarboxylic acid having 6 to 20 carbon atoms) bonded to the ITO particles by the above-described surface modification may be bonded to the ITO particles as it is, a part thereof may be replaced with a group derived from an acidic polymer, or all may be replaced with groups derived from acidic polymers. In the resin composition according to the embodiment of the present invention, it is preferable that both a group derived from a monocarboxylic acid having 6 to 20 carbon atoms and a group derived from an acidic polymer are bonded to the surface of the ITO particles.

As the solvent, a solvent having a constituent ($\delta p$) of 0 to 6 $MPa^{(1/2)}$, the constituent being a polarity term in the SP value, is preferable.

The constituent ($\delta p$) of polarity term in the SP value is a value calculated by the Hansen solubility parameter. The Hansen solubility parameter is constituted of intermolecular dispersive force energy ($\delta d$), intermolecular polar energy ($\delta p$), and intermolecular hydrogen bonding energy ($\delta h$). In the present specification, the Hansen solubility parameter is a value calculated using HSPiP (version 4.1.07) software.

Specifically, the solvent is preferably toluene (1.4), xylene (1.0), or hexane (0), and more preferably toluene. The value in the parentheses is a value of $\delta p$.

A method for producing the ITO particles is not particularly limited, and for example, the ITO particles can be produced according to the procedure described in ACS Nano 2016, 10, pp. 6942 to 6951. According to the procedure of the reference, a dispersion liquid of surface-modified ITO particles is obtained.

Specifically, a solution obtained by mixing a monocarboxylic acid having 6 to 20 carbon atoms, an indium salt (for example, indium acetate), and a tin salt (for example, tin acetate) is added dropwise to an alcohol (long-chain alcohol such as oleyl alcohol) heated to high temperature, and the mixture is retained at high temperature, thereby capable of forming particles. Thereafter, a poor solvent (lower alcohol such as ethanol) having low polymer solubility is added thereto to precipitate the particles, the supernatant is removed, and the particles are redispersed in the above-described solvent such as toluene, thereby capable of forming a dispersion liquid of surface-modified ITO particles.

In the resin composition according to the embodiment of the present invention, the content of the ITO particles is preferably 15% by mass to 40% by mass, more preferably 20% by mass to 38% by mass, and still more preferably 25% by mass to 36% by mass with respect to the total mass (in a case of including a solvent, a mass of solid content excluding the solvent) of the resin composition.

[Indium Tin Oxide Particle Dispersant]

The resin composition according to the embodiment of the present invention preferably includes a dispersant for dispersing ITO particles in the composition. As the dispersant, a cationic type surfactant, a nonionic type surfactant, or a surfactant having both types can be used. Specifically, a dispersant having a carboxylic acid, a phosphoric acid, an amine, a polycarboxylic acid, a polyphosphoric acid, a hydrostearic acid, an amide sulfonic acid, an acrylic acid, a polyacrylic acid, or a salt thereof can be used.

Specific examples thereof include DISPERBYK series (manufactured by BYK Japan KK) such as DISPERBYK-106, 108, 110, 111, 118, 140, 142, 145, 161, 162, 163, 164, 167, 168, 180, 2013, 2055, and 2155, and Phosmer series (manufactured by Unichemical Co., Ltd.) such as Phosmer M, Phosmer PE, Phosmer MH, and Phosmer PP. However, the dispersant of the present is not limited to these.

The content of the dispersant in the resin composition according to the embodiment of the present invention is preferably 5% by mass to 40% by mass, more preferably 6% by mass to 30% by mass, and still more preferably 7% by mass to 20% by mass with respect to the total mass of ITO particles in the resin composition.

<Other Components>

The resin composition may further include other components in addition to the near-ultraviolet light-absorbing organic compound, ITO particles, and dispersant. Specific examples of the other components include at least one selected from a (meth)acrylate monomer, a polymer, a photoradical polymerization initiator, and a thermal radical polymerization initiator.

[(Meth)Acrylate Monomer]

The resin composition may include a (meth)acrylate monomer. In particular, in a case where the near-ultraviolet light-absorbing organic compound is a polymerizable compound, it is preferable that the resin composition is a curable composition by including a (meth)acrylate monomer. The (meth)acrylate monomer may be a polyfunctional (meth)acrylate monomer having two or more (meth)acryloyl groups in the molecule, or may be a monofunctional (meth)acrylate monomer having one (meth)acryloyl group in the molecule.

Specific examples of the (meth)acrylate monomer include the following monomer 1 (phenoxyethyl acrylate), monomer 2 (benzyl acrylate), monomer 3 (tricyclodecanedimethanol diacrylate), monomer 4 (dicyclopentanyl acrylate), and (meth)acrylate monomers described in paragraphs 0037 to 0046 of JP2012-107191A. The molecular weight of the (meth)acrylate monomer is preferably 100 to 500.

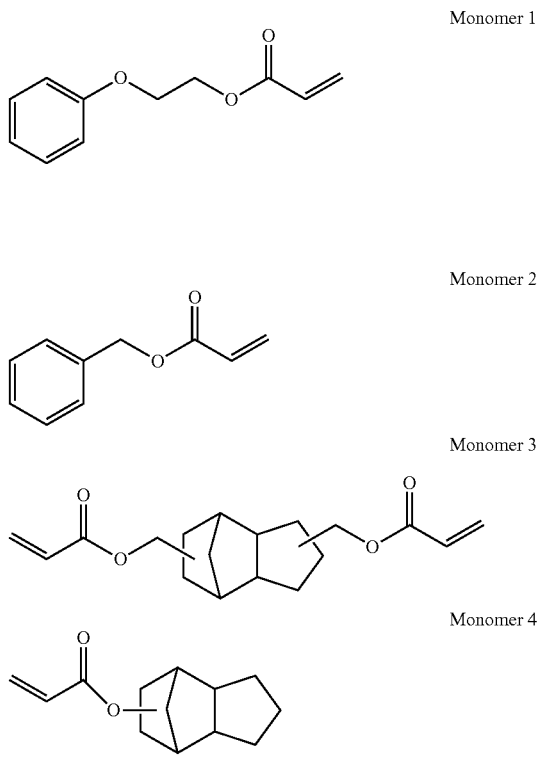

The method for obtaining the (meth)acrylate monomer is not particularly limited, and the (meth)acrylate monomer may be obtained commercially or may be produced synthetically. In a case of being obtained commercially, for example, Viscoat #192 PEA (monomer 1) (manufactured by OSAKA ORGANIC CHEMICAL INDUSTRY LTD.), Viscoat #160 BZA (monomer 2) (manufactured by OSAKA ORGANIC CHEMICAL INDUSTRY LID.), A-DCP (monomer 3) (manufactured by Shin-Nakamura Chemical Co., Ltd.), and FA-513AS (monomer 4) (manufactured by Hitachi Chemical Co., Ltd.) can be preferably used.

In addition, in a case where it is necessary to increase the hardness and rub resistance of the surface of the cured product, the resin composition preferably includes a polyfunctional (meth)acrylate monomer having three or more (meth)acryloyl groups in the molecule. By including a polyfunctional (meth)acrylate monomer having three or more (meth)acryloyl groups in the molecule, the crosslink density of the cured product can be effectively improved, so that the surface hardness and rub resistance can be increased while maintaining a high partial dispersion ratio. The upper limit of the number of (meth)acryloyl groups in the polyfunctional (meth)acrylate monomer having three or more (meth)acryloyl groups in the molecule is not particularly limited, but is preferably 8 and more preferably 6. In a case of being obtained commercially, for example, A-TMPT (monomer 5), A-TMMT (monomer 6), AD-TMP (monomer 7), and A-DPH (monomer 8) (all manufactured by Shin-Nakamura Chemical Co., Ltd.) can be preferably used.

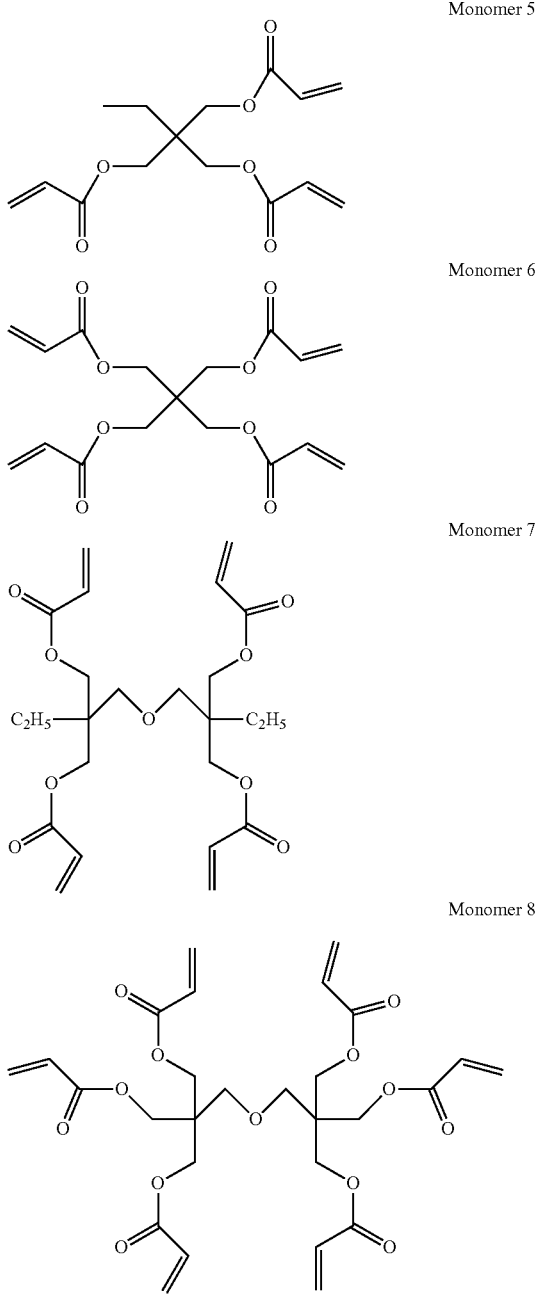

Monomer 5

Monomer 6

Monomer 7

Monomer 8

In a case where the resin composition contains a (meth)acrylate monomer, the content of the (meth)acrylate monomer is preferably 1% to 60% by mass, more preferably 2% to 50% by mass, and still more preferably 3% to 40% by mass with respect to the total mass of the resin composition. In a case where the near-ultraviolet light-absorbing organic compound is not a polymerizable compound, the content of the (meth)acrylate monomer is preferably 20% to 70% by mass, more preferably 30% to 60% by mass, and still more preferably 40% to 50% by mass. The amount of (meth)acrylate monomer in the resin composition can be adjusted to adjust the function of the cured product to relieve stress in a case of thermal change.

In particular, in a case where it is necessary to increase the surface hardness and rub resistance of the cured product, the resin composition includes the polyfunctional (meth)acrylate monomer having three or more (meth)acryloyl groups in the molecule in an amount of preferably 5% to 50% by mass, more preferably 1.0% to 45% by mass, and still more preferably 25% to 40% by mass with respect to the total mass (in a case of including a solvent, a mass of solid content excluding the solvent) of the resin composition. In a case where the near-ultraviolet light-absorbing organic compound is not a polymerizable compound, the content of the above-described (meth)acrylate monomer is preferably 25% to 75% by mass, more preferably 35% to 65% by mass, and still more preferably 45% to 55% by mass.

[Polymer]

The resin composition according to the embodiment of the present invention may further include a polymer in addition to the above-described compounds. In particular, a polymer having a radically polymerizable group has a function of increasing the viscosity of the resin composition, so that the polymer can also be called a thickener or a thickening polymer. The polymer can be added to adjust the viscosity of the resin composition. However, the polymer does not have to include a radically polymerizable group.

Examples of the polymer include a polymer having a radically polymerizable group in the side chain described later, a polyacrylic acid ester, a urethane oligomer, a polyester, and a polyalkylene. Examples of the polyacrylic ester include methyl polyacrylate and butyl polyacrylate. In addition, as the polymer, commercially available products such as LIR-30, 50, 290, 310, 390, and 700 (KURARAY CO., LTD.) can also be used.

(Polymer having Radically Polymerizable Group)

The polymer having a radically polymerizable group may be a homopolymer or a copolymer. It is more preferably a polymer in which a moiety having a radically polymerizable group is introduced into a side chain of polyacrylic acid ester, urethane oligomer, polyester, or polyalkylene.

Examples of the radically polymerizable group include a (meth)acrylate group, a vinyl group, a styryl group, and an allyl group. In the polymer having a radically polymerizable group in the side chain, a repeating unit having a radically polymerizable group is included in an amount of preferably 5% to 100% by mass, more preferably 10% to 90% by mass, and still more preferably 20% to 80% by mass.

Hereinafter, specific examples of the polymer having a radically polymerizable group, which is preferably used in the present invention, will be shown, but the polymer having a radically polymerizable group is not limited to the following structures.

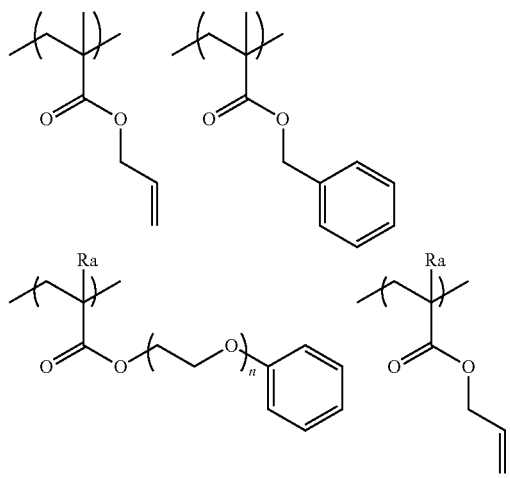

-continued
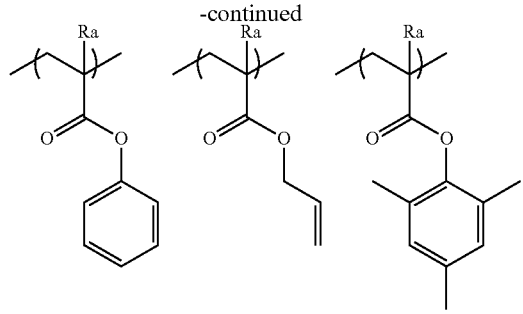
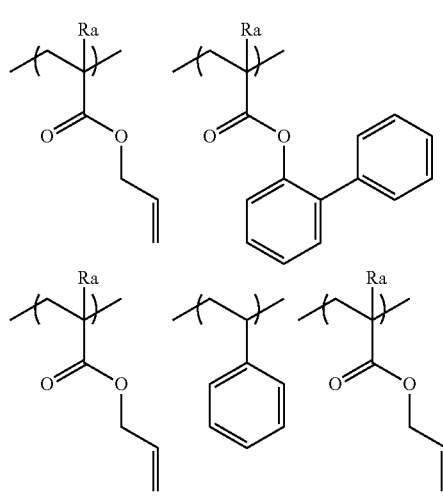
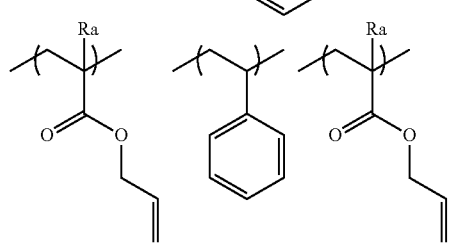
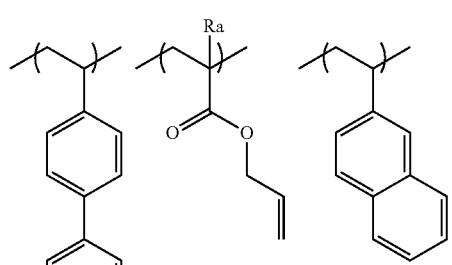
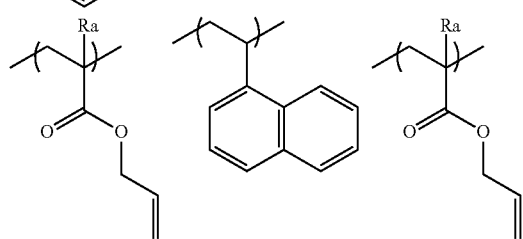
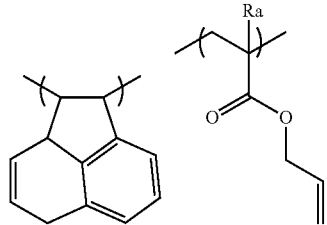
-continued
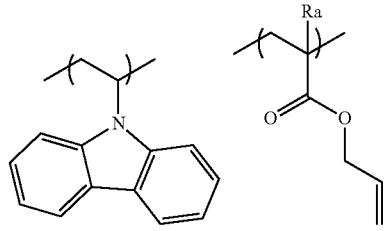
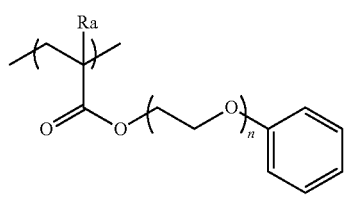
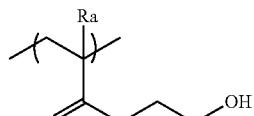
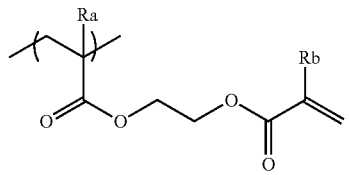
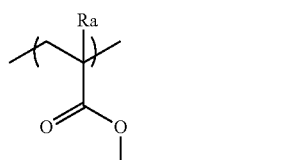
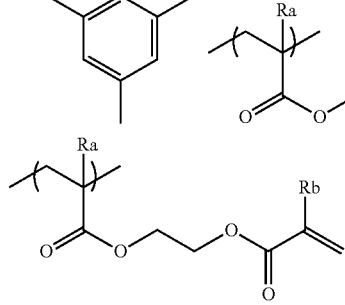
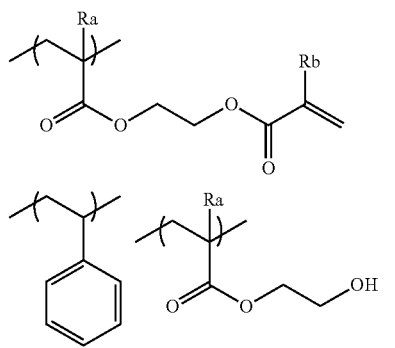

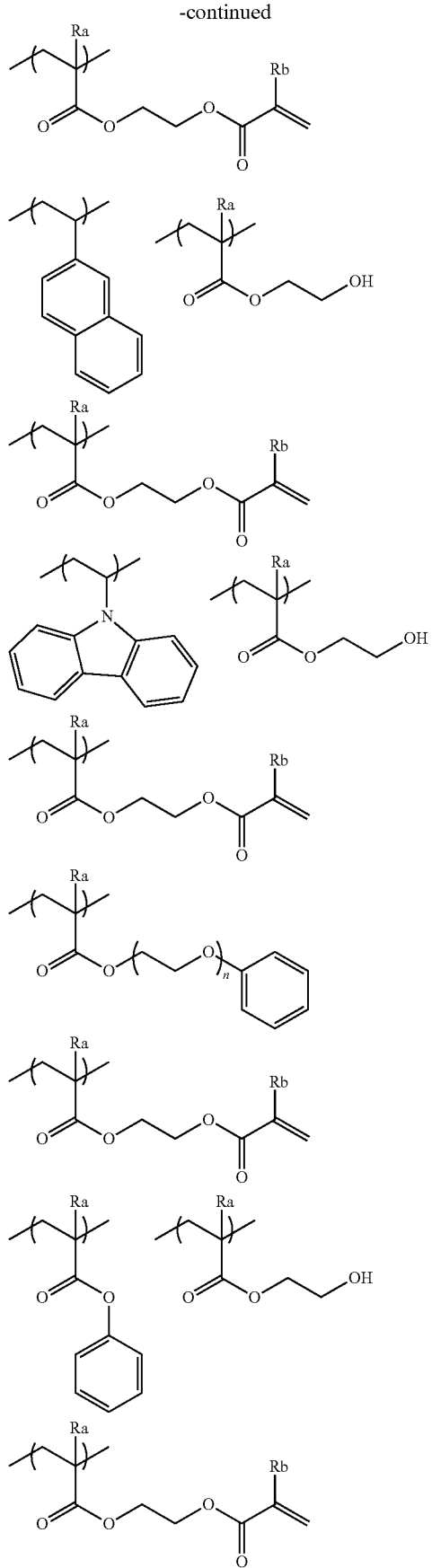
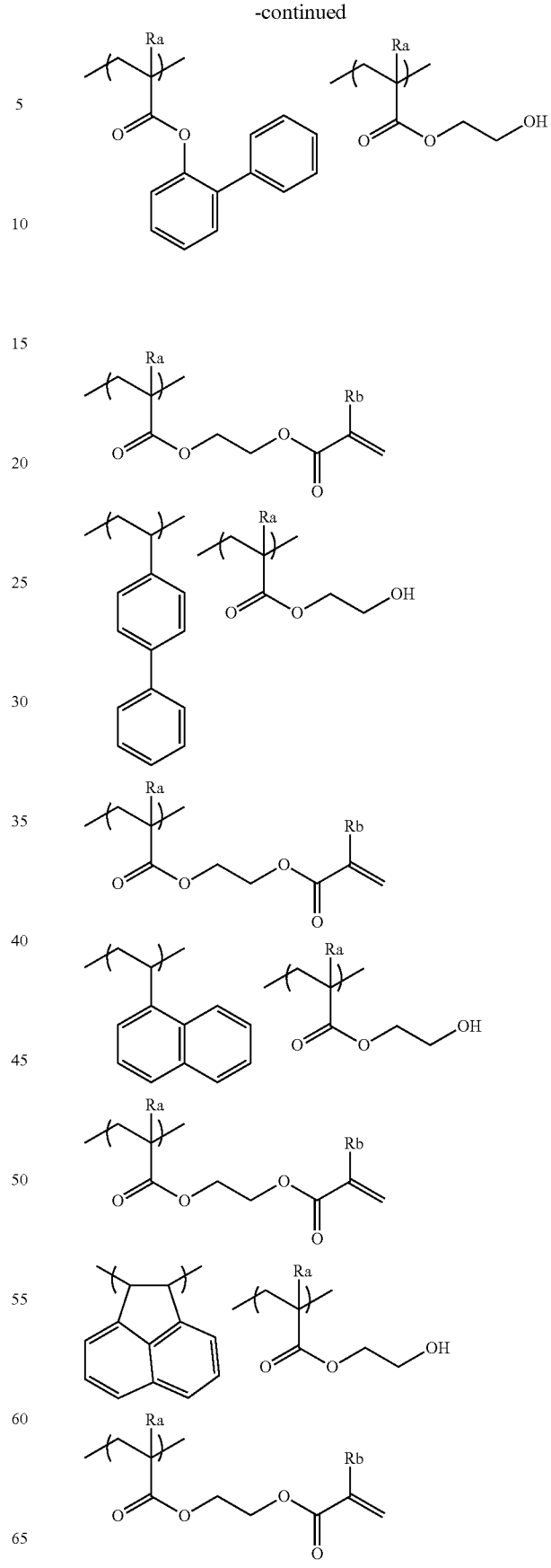

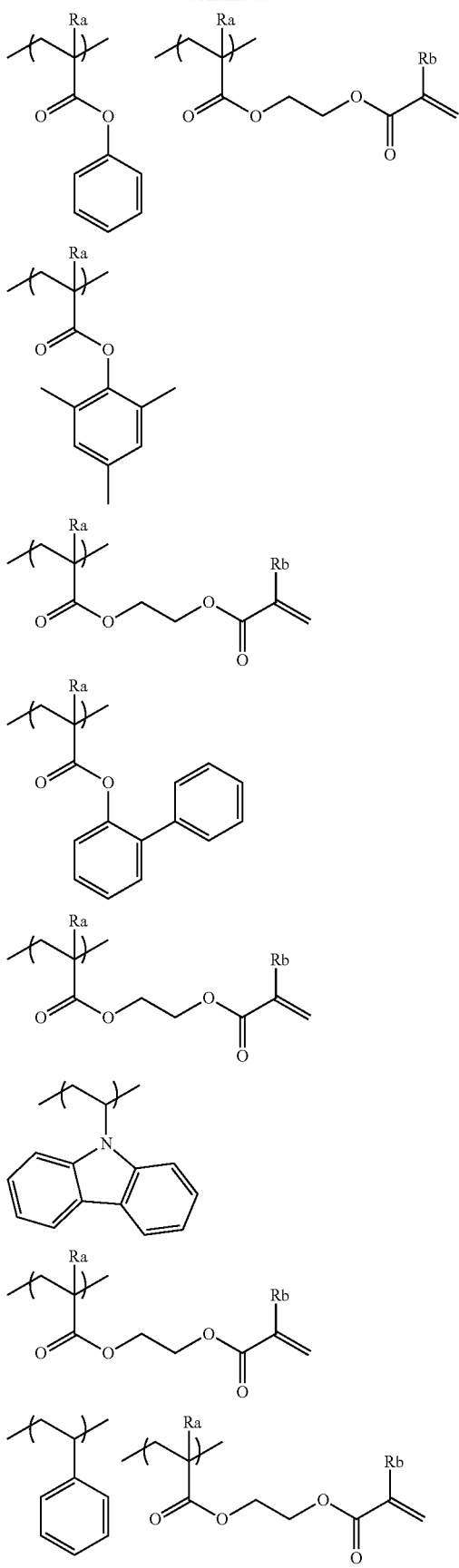

In addition, examples of a commercially available product thereof include UC-102M and 203M (KURARAY CO., LTD.), AA-6, AS-6S, and AB-6 (TOAGOSEI CO., LTD.), Shikou series (The Nippon Synthetic Chemical Industry Co., Ltd.), and EBECRYL270, 8301R, 8402, 8465, and 8804 (DAICEL-ALLNEX LTD.).

The molecular weight (weight-average molecular weight) of the polymer is preferably 1,000 to 10,000,000, more preferably 5,000 to 300,000, and still more preferably 10,000 to 200,000. In addition, the glass transition temperature of the polymer is preferably −50° C. to 400° C. and more preferably −30° C. to 350° C.

The content of the polymer is preferably 40% by mass or less, more preferably 30% by mass or less, and still more preferably 25% by mass or less with respect to the total mass of the resin composition. The content of the polymer may be 0% by mass, and an aspect in which no polymer is added is also preferable.

[Polymerization Initiator]

The resin composition including the compound represented by General Formula 1 preferably includes at least one selected from a thermal radical polymerization initiator or a photoradical polymerization initiator.

(Thermal Radical Polymerization Initiator)

The resin composition preferably includes a thermal radical polymerization initiator. By this action, a cured product having high heat resistance can be molded by thermally polymerizing the resin composition.

Specifically, the following compounds can be used as the thermal radical polymerization initiator. Examples thereof include 1,1-di(t-hexylperoxy) cyclohexane, 1,1-di(t-butylperoxy) cyclohexane, 2,2-di(4,4-di-(t-butylperoxy)cyclohexyl) propane, t-hexylperoxyisopropyl monocarbonate, t-butylperoxy-3,5,5-trimethylhexanoate, t-butylperoxylaurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, t-butylperoxy-2-ethylhexyl, and 2,3-dimethyl-2,3-diphenylbutane.

The content of the thermal radical polymerization initiator is preferably 0.01% to 10% by mass, more preferably 0.05% to 5.0% by mass, and still more preferably 0.05% to 2.0% by mass with respect to the total mass of the resin composition.

(Photoradical Polymerization Initiator)

The resin composition preferably includes a photoradical polymerization initiator. Specifically, the following compounds can be used as the photoradical polymerization initiator. Examples thereof include bis(2,6-dimethoxybenzoyl)-2,4,4-trimethylpentyl phosphine oxide, bis(2,6-dimethylbenzoyl)-2,4,4-trimethylpentyl phosphine oxide, bis(2,4,6-trimethylbenzoyl)-2,4,4-trimethylpentyl phosphine oxide, bis(2,6-dichlorobenzoyl)-2,4,4-trimethylpentyl phosphine oxide, 1-phenyl-2-hydroxy-2-methylpropan-1-one, 1-hydroxycyclohexylphenylketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)-butanone-1,2,4,6-trimethylbenzoyl-diphenyl-phosphine oxide, and bis(2,4,6-trimethylbenzoyl)-phenylphosphine oxide.

Among these, in the present invention, as the photoradical polymerization initiator, IRGACURE 184 (1-hydroxycyclohexylphenylketone), IRGACURE 819 (bis(2,4,6-trimethylbenzoyl)-phenylphosphine oxide), IRGACURE TPO (2,4,6-trimethylbenzoyl-diphenyl-phosphine oxide), and IRGACURE 651 (2,2-dimethoxy-1,2-diphenylethan-1-one), all manufactured by BASF, 1-[4-(2-hydroxyethoxy)-phenyl]-2-hydroxy-2-methyl-1-propan-1-one, and 2-methyl-1-(4-methylthiophenyl)-2-morpholinopropan-1-one can be preferably used.

The content of the photoradical polymerization initiator is preferably 0.01% to 5.0% by mass, more preferably 0.05% to 1.0% by mass, and still more preferably 0.05% to 0.5% by mass with respect to the total mass of the resin composition.

The resin composition preferably includes both photoradical polymerization initiator and thermal radical polymerization initiator. In this case, the total content of the photoradical polymerization initiator and the thermal radical polymerization initiator is preferably 0.01% to 5% by mass, more preferably 0.05% to 1.0% by mass, and still more preferably 0.05% to 0.5% by mass with respect to the total mass of the resin composition.

(Other Additives and the Like)

The resin composition including the near-ultraviolet light-absorbing organic compound may include additives such as a polymer or a monomer other than the above-described components, a dispersant, a plasticizer, a heat stabilizer, a release agent, or the like as long as the gist of the invention is maintained.

<Properties and the Like of Resin Composition>

The viscosity of the resin composition according to the embodiment of the present invention is preferably 5,000 mPa·s or less, more preferably 3,000 mPa·s or less, still more preferably 2,500 mPa·s or less, and particularly preferably 2,000 mPa·s or less. By setting the viscosity of the resin composition within the above-described range, handleability in a case of molding a cured product can be improved, and a cured product having high quality can be formed. The viscosity of the resin composition according to the embodiment of the present invention is preferably 50 mPa·s or more, more preferably 100 mPa·s or more, still more preferably 200 mPa·s or more, and particularly preferably 500 mPa·s or more.

<Cured Product>

The cured product according to an embodiment of the present invention is formed from the above-described resin composition. The cured product is obtained by polymerizing a polymerizable compound (compound represented by General Formula 1, a (meth)acrylate monomer and the like), but the cured product according to the embodiment of the present invention may include an unreacted monomer.

A cured product obtained by curing the resin composition according to the embodiment of the present invention is transparent, has a low Abbe number (vD), and has a low refractive index (nF).

For example, in a case where the above-described cured product is formed into a sheet having a thickness of 6 μm, it is possible to obtain a transmittance of 83% or more at a wavelength of 780 nm. The transmittance means a transmittance measured by a spectrophotometer (for example, a spectrophotometer "V-670" manufactured by JASCO Corporation).

In the present specification, the "refractive index (nF)" is a refractive index at a wavelength of 486.13 nm. In addition, the "Abbe number (vD)" is a value calculated from refractive index measurement values at different wavelengths by the following equation.

$$vD=(nD-1)/(nF-nC)$$

Here, nD represents a refractive index at a wavelength of 587.56 nm, nF represents a refractive index at a wavelength of 486.13 nm, and represents a refractive index at a wavelength of 656.27 nm.

The Abbe number vD of the cured product obtained by curing the resin composition according to the embodiment of the present invention is not particularly limited, but is preferably 30 or less, more preferably 27 or less, still more preferably 25 or less, and particularly preferably 23 or less. In addition, the Abbe number of the above-described cured product is not particularly limited, but is preferably 5 or more, more preferably 10 or more, still more preferably 15 or more, and particularly preferably 17 or more. The Abbe number of the above-described cured product is preferably 15 to 25.

The refractive index nF of the cured product obtained by curing the resin composition according to the embodiment of the present invention is preferably 1.42 to 1.60 and more preferably 1.45 to 1.58.

A birefringence Δn (in the present specification, sometimes referred to as a birefringence Δn(587 nm)) of the cured product of the resin composition according to the embodiment of the present invention at a wavelength of 587 nm is preferably 0.00≤Δn≤0.01. The birefringence Δn(587 nm) is more preferably 0.001 or less and still more preferably less than 0.001. The lower limit value of the birefringence Δn(587 nm) may be 0.00001 or 0.0001.

The birefringence Δn(587 nm) of the cured product can be determined by the following method. A film-shaped sample is produced, and using a birefringence evaluation device (for example, WPA-100 manufactured by Photonic Lattice, Inc.), a birefringence within a 10 mm diameter circle including the center of the sample is measured. Thereafter, the birefringence Δn(587 nm) can be obtained by obtaining the average value of birefringence at a wavelength of 587 nm.

«Use of Resin Composition»

The use of the resin composition according to the embodiment of the present invention is not particularly limited, but is it preferably used as a material for producing a diffractive optical element. In particular, the resin composition according to the embodiment of the present invention is used as a material for producing a low Abbe number diffractive optical element in a multilayer diffractive optical element, and can provide excellent diffraction efficiency.

<Diffractive Optical Element>

A diffractive optical element formed by curing the resin composition according to the embodiment of the present invention preferably has a maximum thickness of 2 μm to 100 μm. The maximum thickness is more preferably 2 to 50 μm and particularly preferably 2 μm to 30 μm. In addition, the level difference of the diffractive optical element is preferably 1 μm to 100 μm and more preferably 1 μm to 50 μm. Furthermore, it is sufficient that the pitch of the diffractive optical element is in a range of 0.1 mm to 10 mm, and it is preferable that the pitch is changed according to the required optical aberration in the same diffractive optical element.

The diffractive optical element can be produced according to, for example, the following procedure.

The resin composition is sandwiched between a surface of a mold, which is processed into a diffraction grating shape, and a transparent substrate, Thereafter, the resin composition may be pressurized and stretched to a desired range. In the sandwiched state, the resin composition is irradiated with light from the transparent substrate side to cure the resin composition. Thereafter, the cured product is released from the mold. After the mold release, the cured product may be further irradiated with light from the side opposite to the transparent substrate side.

Examples of the transparent substrate include a flat glass, and a flat transparent resin (such as (meth)acrylic resin, polycarbonate resin, and polyethylene terephthalate).

The transparent substrate used in the above-described production may be included in the diffractive optical element as it is, or may be peeled off.

The surface of the mold, which is processed into a diffraction grating shape, is preferably a chromium nitride-treated surface. As a result, good mold releasability can be obtained, and the producing efficiency of the diffractive optical element can be improved.

Examples of the chromium nitride treatment include a method for forming a chromium nitride film on the mold surface. As the method for forming a chromium nitride film on the mold surface, a chemical vapor deposition (CVD) method and a physical vapor deposition (PVD) method can be exemplified. The CVD method is a method in which a raw material gas including chromium and a raw material gas including nitrogen are reacted at a high temperature to form a chromium nitride film on a surface of a base substance. In addition, the PVD method is a method (arc-type vacuum vapor deposition method) for forming a chromium nitride film on a surface of a base substance using arc discharge. The arc-type vacuum vapor deposition method is a method for forming a film of a compound by reacting ionized metals with a reaction gas on the surface of the base substance. Specifically, a cathode (evaporation source) formed with, for example, chrome in a vacuum container, is disposed, arc discharge occurs between the cathode and a wall surface of the vacuum container through a trigger, ionization of metal by arc plasma is performed at the same time of evaporating the cathode, a negative voltage is applied to the base substance, and a reaction gas (for example, nitrogen gas) is introduced into the vacuum container at approximately several tens mTorr (1.33 Pa).

As the light used for the light irradiation curing the resin composition, ultraviolet light or visible light preferable and ultraviolet light is more preferable. For example, a metal halide lamp, a low pressure mercury lamp, a high pressure mercury lamp, an ultra-high pressure mercury lamp, a germicidal lamp, a xenon lamp, a light emitting diode (LED) light source lamp, and the like are suitably used. The illuminance of ultraviolet light used for the light irradiation curing the resin composition is preferably 1 to 100 mW/cm$^2$, more preferably 1 to 75 m W/cm$^2$, and still more preferably 5 to 50 mW/cm$^2$. The curable resin composition may be irradiated with ultraviolet light having different illuminance multiple times. The exposure dose of ultraviolet light is preferably 0.4 to 10 J/cm$^2$, more preferably 0.5 to 5 J/cm$^2$, and still more preferably 1 to 3 J/cm$^2$. The atmosphere during the light irradiation is preferably an atmosphere replaced with air or an inert gas, and more preferably an atmosphere in which air is replaced with nitrogen until the oxygen concentration is 1% or less.

<Multilayer Diffractive Optical Element>

It is preferable that a multilayer diffractive optical element is formed by including, as a first diffractive optical element, the diffractive optical element formed by curing the resin composition according to the embodiment of the present invention, and further overlapping a second diffractive optical element formed of a different material such that the first diffractive optical element and the second diffractive optical element face each other in lattice-shaped surfaces. In this case, it is preferable that the lattice-shaped surfaces are in contact with each other.

By forming the second diffractive optical element with a material having a higher refractive index and higher Abbe number than the first diffractive optical element, it is possible to suppress the occurrence of flare, and the like, and sufficiently utilize a chromatic aberration reducing effect of the multilayer diffractive optical element.

The Abbe number vD of the second diffractive optical element is not particularly limited, but is preferably more than 30, more preferably 35 or more, and still more preferably 40 or more. In addition, the Abbe number of the second diffractive optical element is not particularly limited, but is preferably 70 or less, more preferably 60 or less, and still more preferably 50 or less.

The refractive index nF of the second diffractive optical element is preferably 1.55 to 1.70 and more preferably 1.56 to 1.65. In addition, the refractive index nF of the second diffractive optical element is set to be larger than the refractive index nF of the first diffractive optical element used simultaneously in the multilayer diffractive optical element.

The material for forming the second diffractive optical element is not particularly limited as long as a cured product having a high refractive index and a high Abbe number is obtained. For example, a resin composition including a (meth)acrylate monomer having a sulfur atom, a halogen atom, an aromatic structure, a resin composition including zirconium oxide and a (meth)acrylate monomer, and the like can be used.

The multilayer diffractive optical element can be produced according to, for example, the following procedure.

A material for forming the second diffractive optical element is sandwiched between a diffraction grating shape surface (surface obtained after the mold release) of a diffractive optical element formed by curing the resin composition according to the embodiment of the present invention, and a transparent substrate. Thereafter, the material may be pressurized and stretched to a desired range. In the sandwiched state, the material is irradiated with light from the transparent substrate side to cure the material. Thereafter, the cured product is released from the mold.

Examples of the transparent substrate include the same examples as the transparent substrate used in a case of producing the diffractive optical element (first diffractive optical element).

The transparent substrate used in the above-described production may be included in the multilayer diffractive optical element as it is, or may be peeled off.

The multilayer diffractive optical element preferably has a maximum thickness of 50 μm to 20 mm. The maximum thickness is more preferably 50 μm to 10 mm and particularly preferably 50 μm to 3 mm.

<Lens>

The above-described diffractive optical element and multilayer diffractive optical element can be used as a lens, respectively.

A film or a member can be provided on the surface or the periphery of the lens depending on the environment in which the lens is used or the use of the lens. For example, a protective film, an anti-reflection film, a hard coat film, and the like can be formed on the surface of the lens. In addition, the lens can be used as a composite lens in which a glass lens or a plastic lens is laminated on the lens. Furthermore, the periphery of the lens can be fitted into a base material holding frame or the like, and fixed. However, these films, frames, and the like are members added to the lens, and are distinguished from the lens itself in the present specification.

The lens is preferably used as an image pick-up lens in a mobile phone, a digital camera, and the like, an imaging lens in a television, a video camera, and the like, and an in-vehicle lens.

EXAMPLES

Features of the present invention will be described in more detail with reference to Examples and Comparative Examples. The materials, amounts used, proportions, treatment details, treatment procedures, and the like described in the following examples can be appropriately modified as long as the gist of the invention is maintained. Therefore, the scope of the present invention should not be construed as being limited to the following specific examples.

<Synthesis of Near-Ultraviolet Light-Absorbing Organic Compound>

Synthesis Example 1

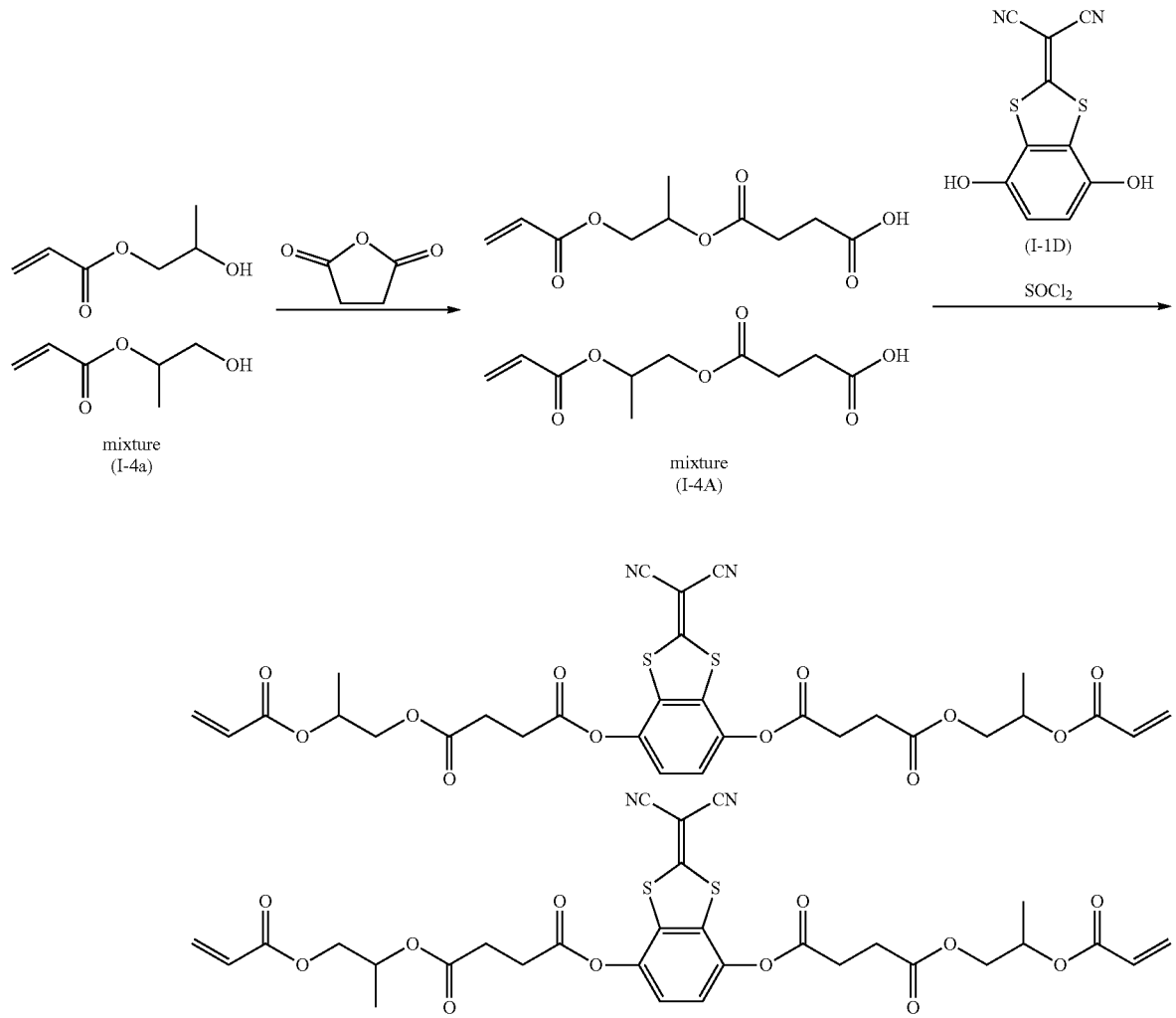

-continued

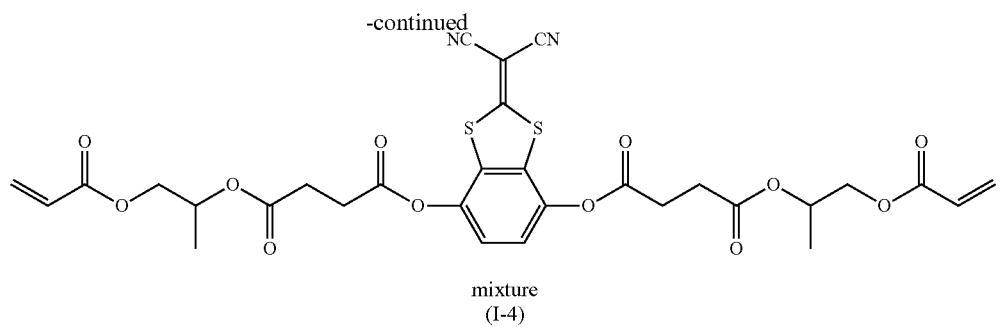

mixture
(I-4)

<Synthesis of Compound (I-1D)>
The synthesis of a compound (1-1D) was performed according to the method described in "Journal of Chemical Crystallography" (1997); 27 (9); pp. 515 to 526.

<Synthesis of Compound (I-4A)>
A compound (I-4A) was synthesized according to the method for synthesizing a compound (I-4A) described in JP2016-81035A.

<Synthesis of Compound (I-4)>
15.5 g (67.4 mmol) of the carboxylic acid compound (I-4A), 183 mL of ethyl acetate, 46 mL, of N,N-dimethylacetamide, and 60 mg of 2,6-di-t-butyl-4-methylphenol were mixed, and the internal temperature was cooled to 0° C. To the mixture, 7.75 g (65.1 mmol) of thionyl chloride was added dropwise at an internal temperature of 0° C. to 5° C. After stirring at 5° C. for 60 minutes, a solution of 6.85 g (27.6 mmol) of the compound (I-1D) and 52 mL of tetrahydrofuran (THF) was added dropwise thereto at an internal temperature of 0° C. to 8° C.

Thereafter, 16.8 g of N,N-diisopropylethylamine was added dropwise thereto at an internal temperature of 0° C. to 10° C. After stirring at an internal temperature of 20° C. to 25° C. for 1 hour, 40 mL of ethyl acetate, 165 mL of water, and 14 mL of concentrated hydrochloric acid were added thereto for washing. The organic layer was washed with 140 mL of saturated saline and separated, and then washed with 100 mL of saturated saline and 10 mL of 7.5% by mass sodium hydrogen carbonate aqueous solution and separated. Thereafter, the organic layer was concentrated to obtain an oily composition, and then the oily composition was purified by column chromatography to obtain a compound (1-4) (yield: 85%). $^1$H-NMR (400 MHz, CDCl$_3$): δ (ppm) 1.25 to 1.35 (d, 6H), 2.78 (t, 4H), 2.95 (t, 4H), 4.10 to 4.35 (m, 4H), 5.25 (sext, 2H), 5.83 (d, 2H), 6.05 to 6.15 (m, 2H), 6.40 (d, 2H), 7.33 (s, 2H)

Synthesis Example 2

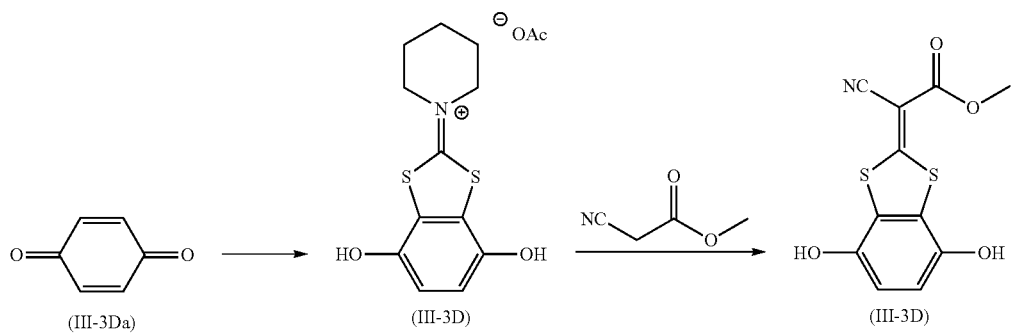

-continued
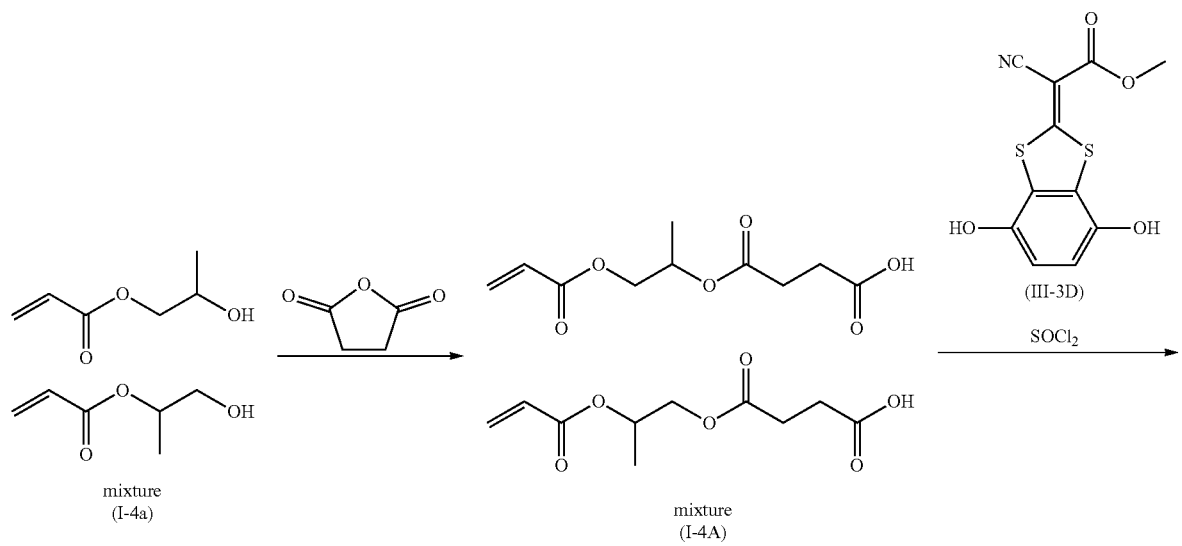
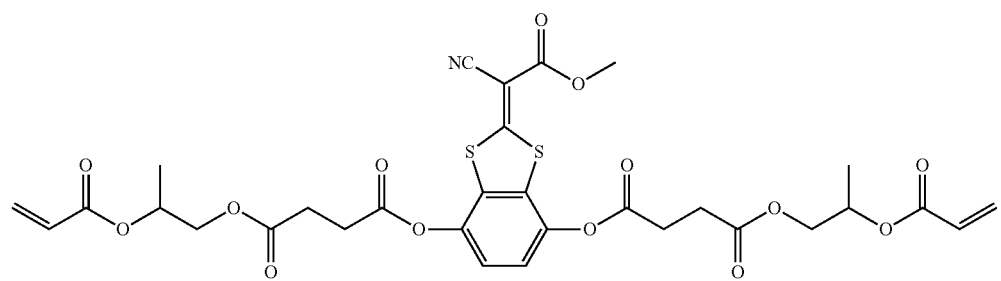
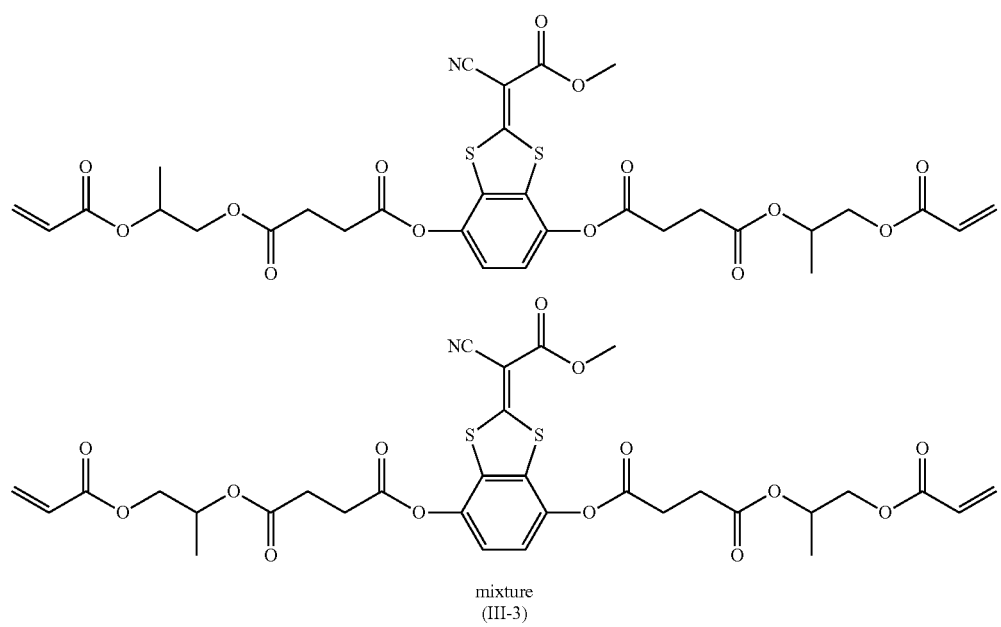
mixture
(III-3)

<Synthesis of Compound (III-3Db)>

The synthesis of a compound (III-3Db) was performed according to the method described in "Journal of Organic Chemistry" (2004); 69 (6); pp. 2164 to 2177.

<Synthesis of Compound (III-3D)>

5.0 g (15.3 mmol) of the compound (III-3Db), 1.66 g (16.80 mmol) of methyl cyanoacetate, and 25 mL of isopropyl alcohol were mixed, and the mixture was stirred while heating under reflux for 3 hours. Thereafter, the mixture was cooled to room temperature, 50 mL of water was added to the mixture, and the precipitated crystals were filtered. The obtained crystals were washed with a mixed solution of water-isopropyl alcohol (10:1) and a 0.5 N hydrochloric acid solution, and then dissolved in N,N-dimethylacetamide and filtered. Water was added to the obtained filtrate, and the precipitated crystals were filtered to obtain 2.2 g (7.82 mmol) of a compound (III-3D) (yield: 51%).

<Synthesis of Compound (III-3)>

A compound (III-3) was obtained in the same manner as in Example 1, except that the compound (I-1D) in the method for synthesizing the compound (I-4) described in Example 1 was changed to the compound (III-3D) (yield: 86%). $^1$H-NMR (400 MHz, CDCl$_3$): δ (ppm) 1.25 to 1.35 (d, 6H) 2.78 (t, 4H), 2.95 (t, 4H), 3.89 (s, 3H), 4.10 to 4.35 (m, 4H), 5.25 (sext, 2H), 5.83 (d, 2H), 6.05 to 6.15 (m, 2H), 6.40 (d, 2H), 7.28 (s, 2H)

Synthesis Example 3

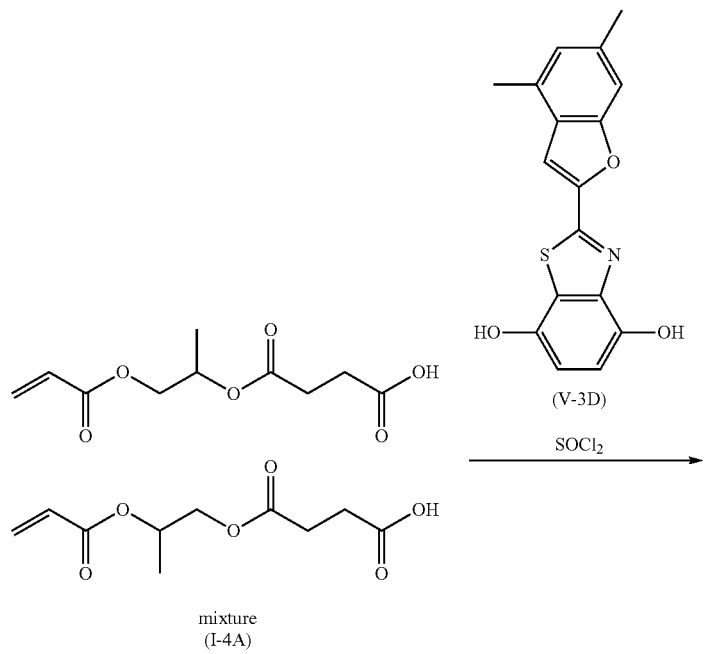

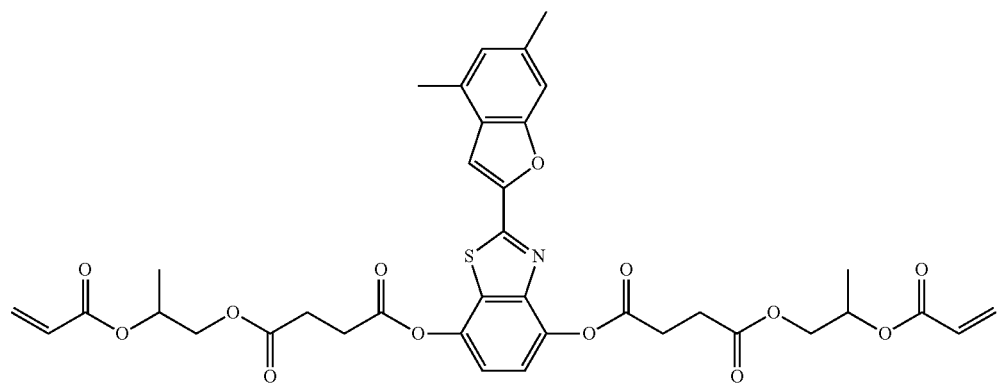

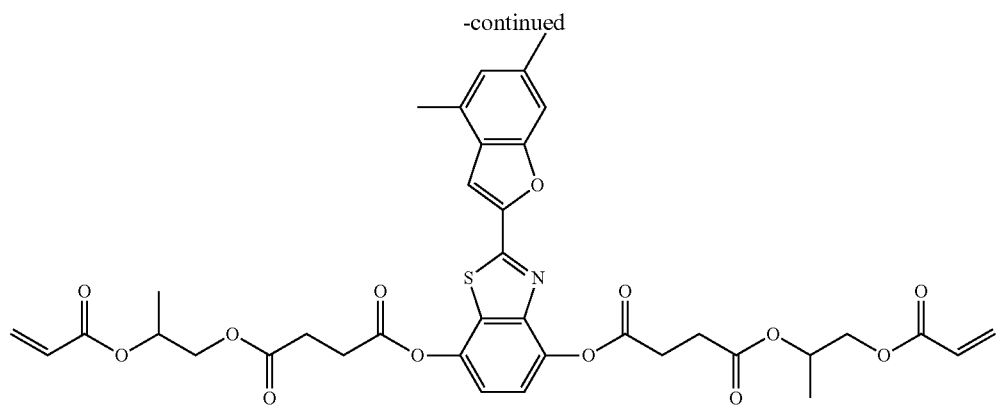

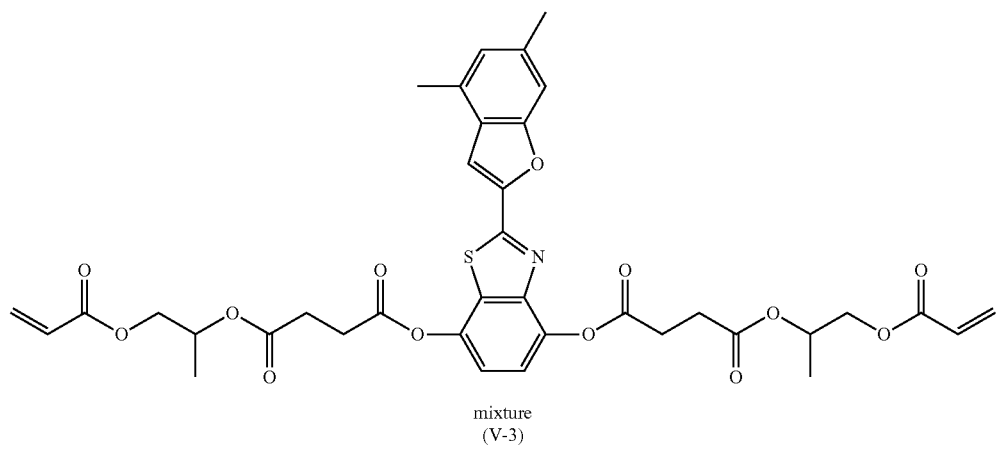

mixture
(V-3)

<Synthesis of V-3D>

The synthesis of a compound (V-3D) was performed with reference to the method for synthesizing a compound (11-d) described in paragraph 0282 of JP2013-71956A.

<Synthesis of Compound (V-3)>

A compound (V-3) was obtained in the same manner as in Example 1, except that the compound (I-1D) in the method for synthesizing the compound (I-4) described in Example 1 was changed to the compound (V-3D) (yield: 82%).

$^1$H-NMR (400 MHz, DMSO-d6): δ (ppm) 1.25 to 1.35 (d, 6H), 2.78 (t, 4H), 2.95 (t, 4H), 4.10 to 4.35 (m, 4H), 5.25 (sext, 2H), 5.83 (d, 2H), 6.05 to 6.15 (m, 2H), 6.40 (d, 2H), 7.03 (s, 1H), 7.35 to 7.45 (m, 3H), 7.80 (s, 1H)

Synthesis Example 4

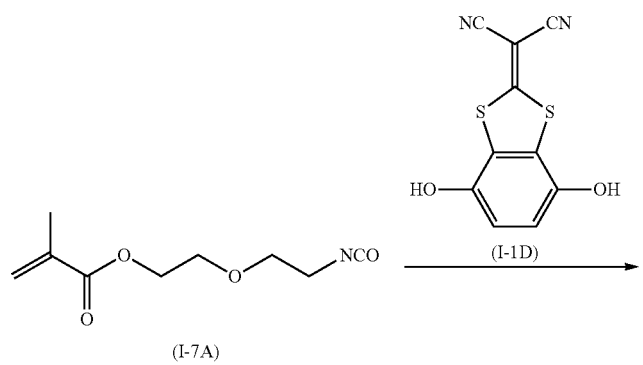

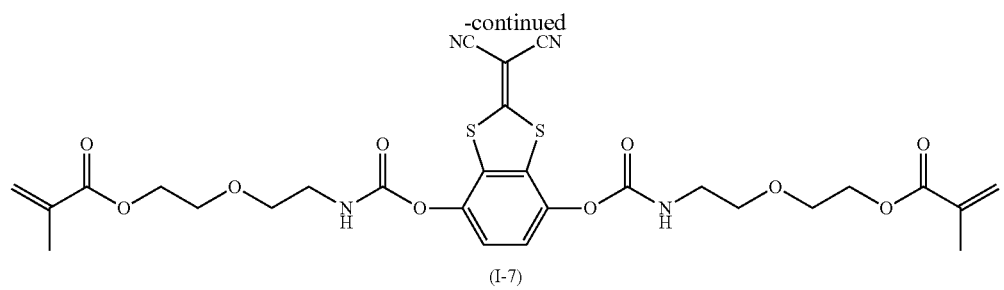

<Synthesis of Compound (I-7)>

3.9 g (19.5 mmol) of Karenz MOI-EG (I-7A, manufactured by SHOWA DENKO K.K.), 2.7 g (10.9 mmol) of the compound (I-1D), 2 mL of N,N-dimethylacetamide, and 20 mL of chloroform were mixed, and the internal temperature was heated to 60° C. After stirring for 12 hours, the mixture was cooled to room temperature and further stirred for 12 hours. Next, a saturated sodium hydrogen carbonate aqueous solution was added thereto, and the mixture was stirred for 1 hour and separated. The collected organic layer was washed with 1N hydrochloric acid and saturated saline, dried over anhydrous sodium sulfate, the solvent was removed with a rotary evaporator, and the resultant was purified by silica gel chromatography to obtain 5.7 g (8.90 mmol) of a compound (I-7) (yield: 82%).

$^1$H-NMR (400 MHz, CDCl$_3$): δ (ppm) 1.95 (s, 6H), 3.37 (m, 4H), 3.60 to 3.70 (m, 8H), 4.20 (t, 4H), 5.15 (br, s, 2H), 5.58 (s, 2H), 6.13 (s, 2H), 7.32 (s, 2H)

Synthesis Example 5

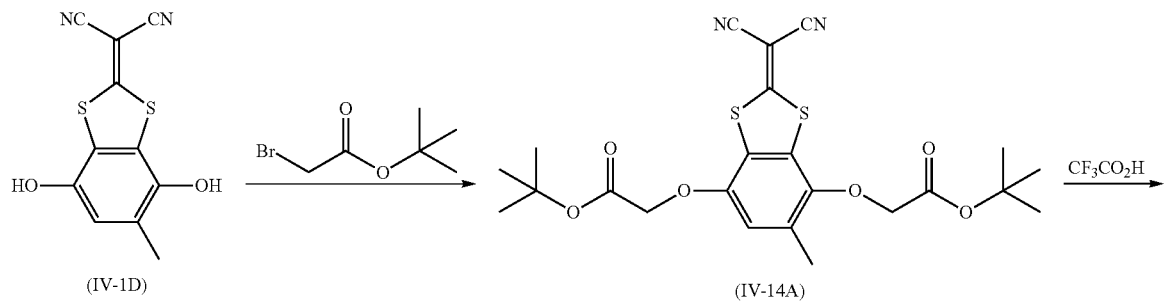

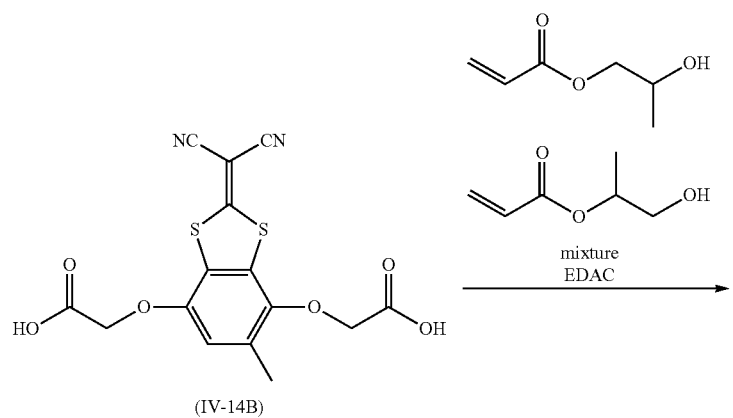

-continued

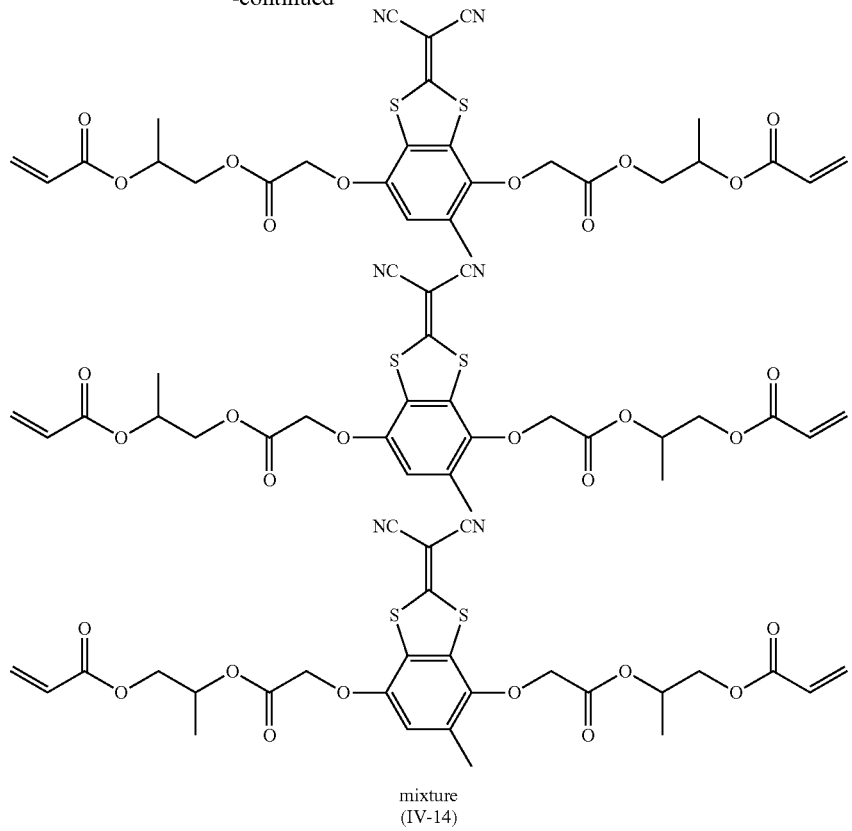

mixture
(IV-14)

<Synthesis of Compound (IV-14A)>
55.8 g (285.9 mmol) of t-butyl bromoacetate, 30 g (114.4 mmol) of a compound (IV-1D), 111.8 g (343.1 mmol) of cesium carbonate, 3.7 g (11.4 mmol) of tetrabutylammonium bromide, 300 mL of THF, and 150 mL of N,N-dimethylacetamide were mixed, and the internal temperature was heated to 75° C. After stirring for 5 hours, the mixture was cooled to 25° C., 750 mL of water was added thereto, and the precipitated solid was filtered. The filtrate was washed with water and methanol to obtain a compound (IV-14A) (yield: 92%).

<Synthesis of Compound (IV-14B)>
After mixing 50 g (102 mmol) of a t-butyl ester compound (IV-14A) and 500 mL of dichloromethane, 150 mL of trifluoroacetic acid was added thereto, and the mixture was stirred at 25° C. for 2 hours. The internal temperature was cooled to 5° C., and the precipitated crystals were filtered and then washed with dichloromethane to obtain a compound (IV-14B) (yield: 98%).

<Synthesis of Compound (IV-14)>
33.0 g (87.2 mmol) of a carboxylic acid compound (IV-14B), 500 mL of dichloromethane, 26.1 g (200.6 mmol) of hydroxypropyl acrylate, 1.1 g (8.7 mmol) of N,N-dimethylaminopyridine, and 38.3 g (200.6 mmol) of 1-ethyl-3-(3-dimethylaminopropyl)carbodiimide hydrochloride (abbreviation: EDAC) were mixed. After stirring at 40° C. for 2 hours, 300 ml of 1N hydrochloric acid water was added thereto, and the mixture was washed and separated. An oily composition was obtained by dehydration with magnesium sulfate, filtration, concentration, and then purified by column chromatography (yield: 60%).

$^1$H-NMR (400 MHz, CDCl$_3$): δ (ppm) 1.25 to 1.35 (d, 6H), 2.36 (s, 3H), 4.10 to 4.30 (m, 2H), 4.30 to 4.45 (m, 2H), 4.52 (d, 2H), 4.72 (d, 2H), 5.20 to 5.40 (m, 2H), 5.83 (m, 2H), 6.05 to 6.15 (m, 2H), 6.40 (d, 2H), 6.65 (d, 1H)

Synthesis Example 6

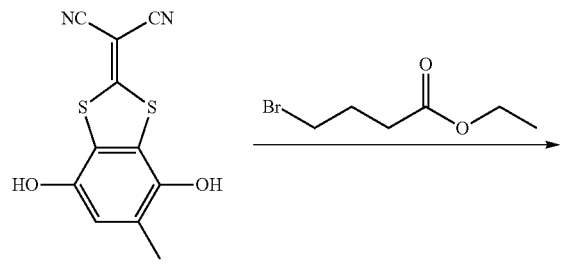

(IV-1D)

-continued
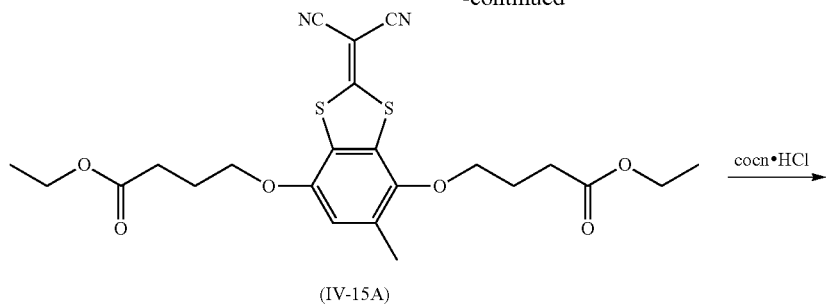
(IV-15A)
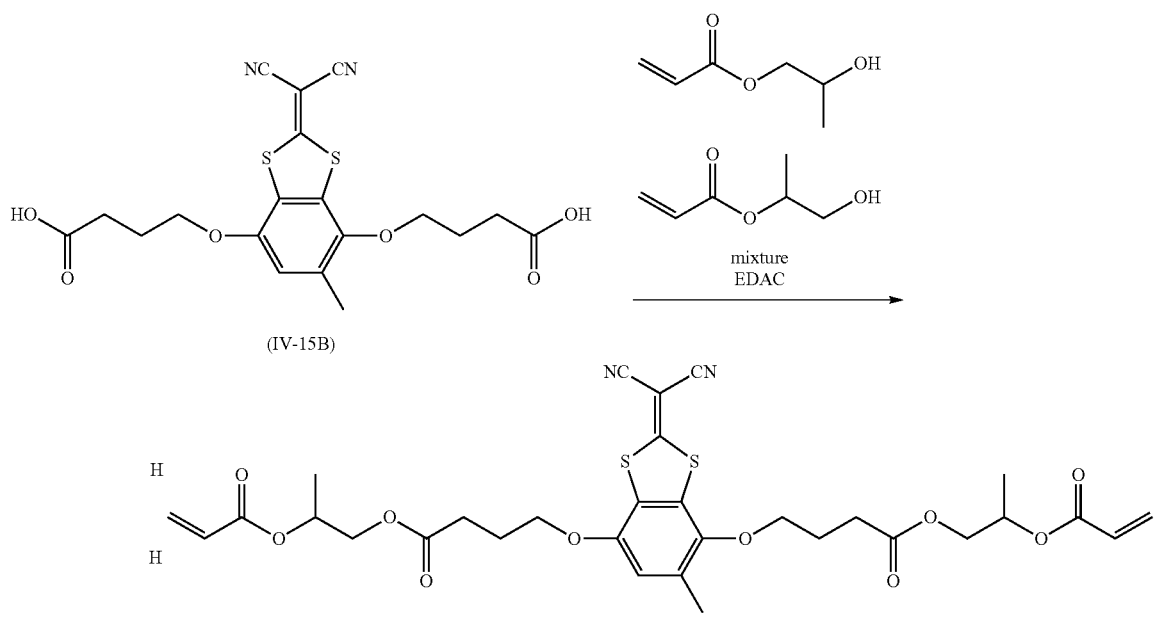
(IV-15B)
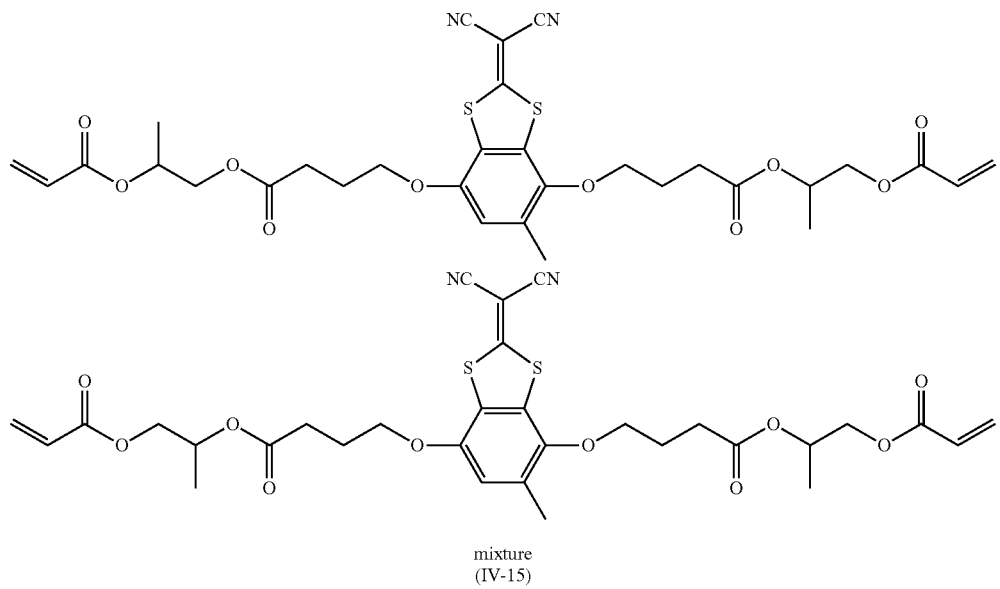
mixture
(IV-15)

<Synthesis of Compound (IV-15A)>

A compound (IV-15A) was obtained in the same manner as in Synthesis Example 11, except that the t-butyl bromoacetate in the method for synthesizing the compound (IV-14A) described in Synthesis Example 11 was changed to ethyl 4-bromoacetate (yield: 75%).

<Synthesis of Compound (IV-15B)>

After mixing 2.5 g (102 mmol) of an ester compound (IV-15A), 5 mL of concentrated hydrochloric acid and 25 mL of acetic acid, the mixture was stirred at 60° C. for 1 hour. Thereafter, 80 mL of water was added thereto, and the precipitated solid was filtered. The obtained solid was purified by column chromatography to obtain a compound (IV-15B) (yield: 80%).

<Synthesis of Compound (IV-15)>

37.9 g (87.2 mmol) of a carboxylic acid compound (IV-15B), 500 mL of dichloromethane, 26.1 g (200.6 mmol) of hydroxypropyl acrylate, 1.1 g (8.7 mmol) of N,N-dimethylaminopyridine, and 38.3 g (200.6 mmol) of 1-ethyl-3-(3-dimethylaminopropyl)carbodiimide hydrochloride (abbreviation: EDAC) were mixed. After stirring at 40° C. for 2 hours, 300 ml of 1N hydrochloric acid water was added thereto, and the mixture was washed and separated. An oily composition was obtained by dehydration with magnesium sulfate, filtration, concentration, and then purified by column chromatography (yield: 55%).

$^1$H-NMR (400 MHz, CDCl$_3$): δ (ppm) 1.20 to 1.35 (m, 6H), 2.10 to 2.20 (m, 4H), 2.32 (s, 3H), 2.60 to 2.75 (m, 4H), 3.91 (t, 2H), 4.10 to 4.30 (m, 6H), 5.24 (sext, 2H), 5.84 (d, 2H), 6.05 to 6.15 (m, 2H), 6.40 (d, 2H), 6.70 (s, 1H)

Synthesis Example 7

<Synthesis of Compound (IV-16)>

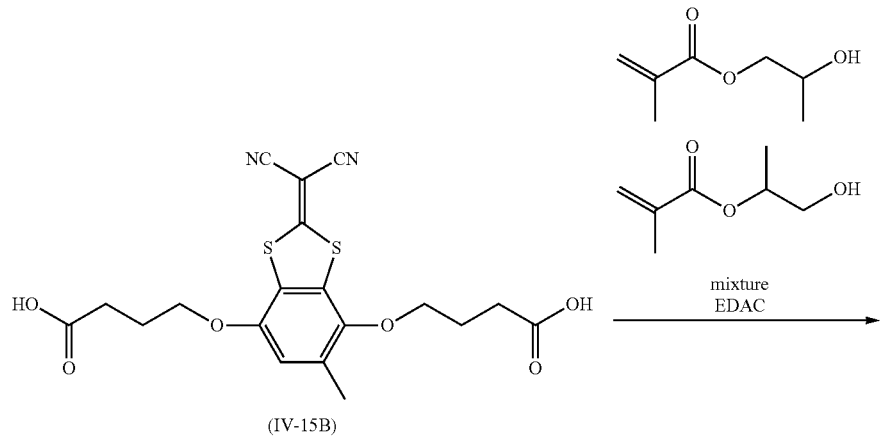

(IV-15B)

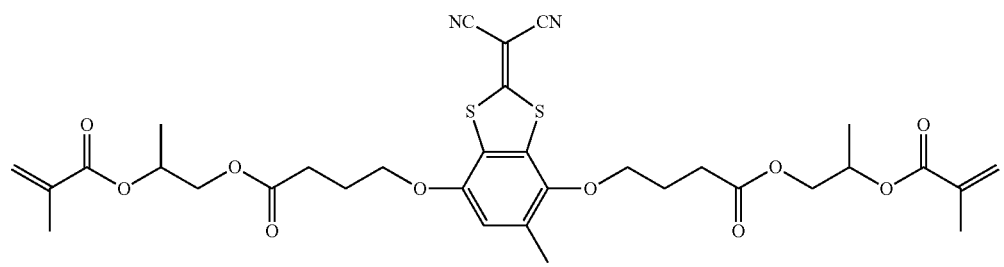

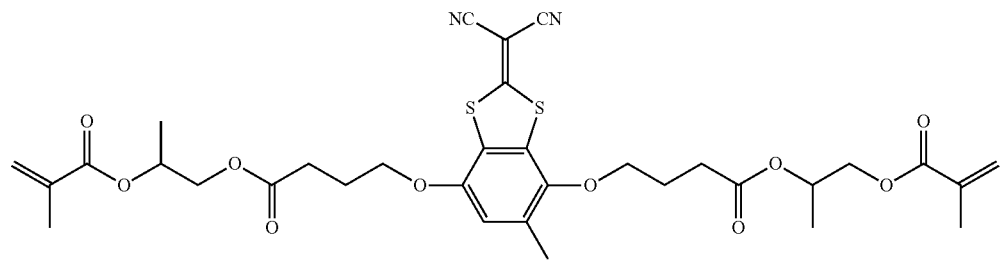

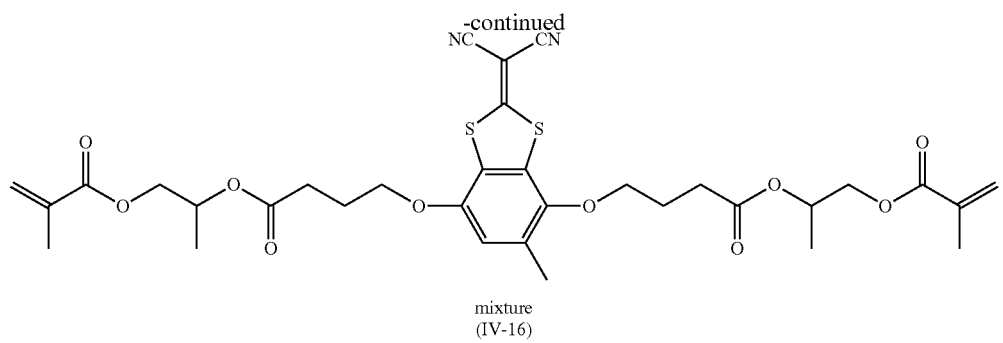

mixture
(IV-16)

A compound (IV-16) was obtained in the same manner as in Synthesis Example 14, except that the hydroxypropyl acrylate in the method for synthesizing the compound (IV-15) described in Synthesis Example 14 was changed to hydroxypropyl methacrylate (yield: 57%).

$^1$H-NMR (400 MHz, CDCl$_3$): δ (ppm) 1.20 to 1.35 (m, 6H), 1.93 (s, 6H), 2.10 to 2.20 (m, 4H), 2.32 (s, 3H), 2.60 to 2.75 (m, 4H), 3.92 (t, 2H), 4.10 to 4.30 (m, 6H), 5.15 to 5.35 (m, 2H), 5.57 (s, 2H), 6.10 (s, 2H), 6.69 (s, 1H)

Absorption spectra (absorbance) of the compounds produced above and a compound C-1 used in the following comparative example were measured by the following procedure.

Each compound was precisely weighed in an amount of 50 mg, diluted with tetrahydrofuran (THF) using a 5 mL volumetric flask, and further diluted with THF so that the solution concentration was 1/500 times to obtain a measurement solution. The measurement was performed using UV-2550 manufactured by Shimadzu Corporation. First, a square quartz cell (cell length: 10 mm) containing a control sample (THF) in both the sample optical path and the control optical path was placed, and the absorbance in a wavelength range of 250 to 800 nm was adjusted to zero. Next, the sample in the sample optical path-side cell was replaced with a solution of the near-ultraviolet light-absorbing organic compound, and the absorption spectrum at 250 to 800 nm was measured, None of the compounds exhibited substantially light absorption at a wavelength of 410 to 800 nm. Table 1 shows the maximum absorbance Abs(λ max) at 340 nm to 400 nm, the absorbance at 410 nm and 430 nm, and the values of each expression obtained from the measurement results. In addition, the absorption spectra of the compound IV-15 and the compound C-1 at a wavelength of 250 to 450 nm are shown in FIG. 1.

TABLE 1

| Compound | V-3 | I-4 | III-3 | I-7 | IV-14 | IV-15 | IV-16 | C-1 |
|---|---|---|---|---|---|---|---|---|
| λmax/mn | 351 | 353 | 362 | 355 | 372 | 374 | 374 | 310 |
| Abs(λmax) | 0.882 | 0.689 | 0.733 | 0.748 | 0.773 | 0.727 | 0.720 | 0.235 |
| Abs(410 mm) | 0.000 | 0.000 | 0.000 | 0.000 | 0.003 | 0.005 | 0.005 | 0.000 |
| Abs(430 mm) | 0.000 | 0.000 | 0.000 | 0.000 | 0.000 | 0.001 | 0.001 | 0.000 |
| PA-1 | 1.00 | 1.00 | 1.00 | 1.00 | 1.00 | 0.99 | 0.99 | 1.00 |
| PA-2 | 1.00 | 1.00 | 1.00 | 1.00 | 1.00 | 0.99 | 0.99 | 1.00 |
| P1 | 0.015 | 0.012 | 0.015 | 0.014 | 0.020 | 0.020 | 0.020 | 0.002 |

In the table, PA-1, PA-2, and P1 are as follows.

PA-1=(Abs(λ max)−Abs(410 nm))/Abs(λ max)

PA-2=(Abs(λ max)−Abs(410 nm))/(Abs(λ max)−Abs (430 nm))

P1(Abs(λ max)−Abs(410 nm))/(410−λ max)

<Synthesis of ITO Particles (ITO-1)>

75 ml of oleic acid (manufactured by Sigma-Aldrich, Inc., technical grade, 90%), 10.060 g (34.5 mmol) of indium acetate (manufactured by Alfa Aesar, 99.99%), and 1.079 g (3.0 mmol) of tin (IV) acetate (manufactured by Alfa Aesar) were added in a flask. The mixture in the flask was heated at 160° C. for 1 hour under an environment of nitrogen flow to obtain a yellow transparent precursor solution.

Subsequently, 90 ml of oleyl alcohol (manufactured by Wako Pure Chemical Corporation, 65% or more) in another flask was heated to 290° in a nitrogen flow. Using a syringe pump, the precursor solution was added dropwise to the heated oleyl alcohol at a rate of 1.75 mL/min. After the completion of the dropwise addition of the precursor solution, the obtained reaction solution was retained at 290° C. for 120 minutes, and thereafter, the heating was stopped and the reaction solution was cooled to room temperature.

After adding ethanol to the obtained reaction solution, centrifugation was performed to precipitate particles. The removal of the supernatant and the redispersion of the particles in toluene were repeated 3 times to obtain a toluene dispersion liquid. (ITO solid content: 4.75% by mass, surface treatment surface-modified component solid content: 0.25% by mass) of ITO particles (ITO-1) coordinated with oleic acid.

In a case where the ITO particles (ITO-1) were observed with TEM, the average particle size was 21 nm.

<Method for Preparing Resin Composition 1-1>

3.1 g of the compound (V-3), 0.28 g of Phosmer PP (manufactured by Unichemical Co., Ltd.), and 3.82 g of 1,6-hexanediol diacrylate (HDDA, manufactured by TOKYO CHEMICAL INDUSTRY CO., LTD.) were added to 58.9 g of a toluene dispersion liquid of ITO-1 to be dissolved. Toluene was distilled off by suction under reduced pressure while heating in a water bath at approximately 70° C. After the distillation, 0.01 g of IRGACURE 819 (manufactured by BASF) was added to the obtained mixture and dissolved, thereby obtaining a resin composition 1-1.

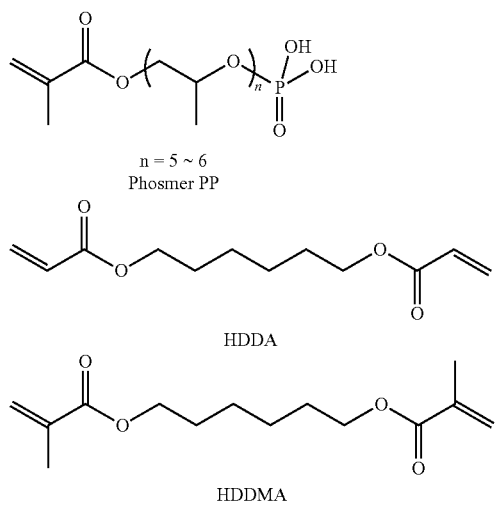

n = 5 ~ 6
Phosmer PP

HDDA

HDDMA

Photocuring Agent

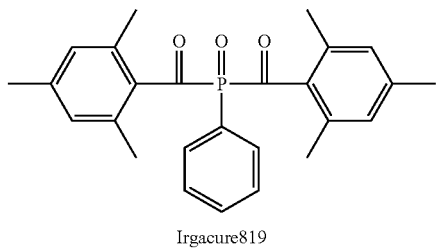

Irgacure819

<Method for Preparing Resin Compositions 1-2 to 1-6>

Resin compositions 1-2 to 1-6 were obtained in the same manner as in the method for preparing the resin composition 1-1, except that the compound (V-3) described in the method for preparing the resin composition 1-1 was changed to the near-ultraviolet light-absorbing organic compound shown in Table 2.

<Method for Preparing Resin Composition 1-7>

3.1 g of the compound (IV-16), 0.28 g of Phosmer PP (manufactured by Unichemical Co., Ltd.), and 3.82 g of 1,6-hexanediol dimethacrylate (HDDMA, manufactured by TOKYO CHEMICAL INDUSTRY CO., LTD.) were added to 58.9 g of a toluene dispersion liquid of ITO-1 to be dissolved. Toluene was distilled off by suction under reduced pressure while heating in a water bath at approximately 70° C. After the distillation, 0.01 g of IRGACURE 819 (manufactured by BASF) was added to the obtained mixture and dissolved, thereby obtaining a resin composition 1-7.

<Method for Preparing Resin Compositions 1-8 to 1-12>

According to the compositional ratio shown in the table, the compound (IV-15), Phosmer PP (manufactured by Unichemical Co., Ltd.), and 1,6-hexanediol diacrylate (HDDA, manufactured by TOKYO CHEMICAL INDUSTRY CO., LTD.) were added to a toluene dispersion liquid of ITO-1 to be dissolved. Toluene was distilled off by suction under reduced pressure while heating in a water bath at approximately 70° C. After the distillation, 0.01 g of IRGACURE 819 (manufactured by BASF) was added to the obtained mixture and dissolved, thereby obtaining resin compositions 1-8 to 1-12.

<Method for Preparing Resin Composition A>

0.43 g of Phosmer PP (manufactured by Unichemical Co., Ltd.) and 53.7 g of 1,6-hexanediol dimethacrylate (HDDMA, manufactured by TOKYO CHEMICAL INDUSTRY CO., LTD.) were added to 90.5 g of a toluene dispersion liquid of ITO-1 to be dissolved. Toluene was distilled off by suction under reduced pressure while heating in a water bath at approximately 70° C. After the distillation, 0.01 g of IRGACURE 819 (manufactured by BASF) was added to the obtained mixture and dissolved, thereby obtaining a resin composition A.

<Method for Preparing Resin Composition B>

0.28 g of Phosmer PP (manufactured by Unichemical Co., Ltd.) and 69.2 g of 1,6-hexanediol dimethacrylate (HDDMA, manufactured by TOKYO CHEMICAL INDUSTRY CO., LTD.) were added to 58.9 g of a toluene dispersion liquid of ITO-1 to be dissolved. Toluene was distilled off by suction under reduced pressure while heating in a water bath at approximately 70° C. After the distillation, 0.01 g of IRGACURE 819 (manufactured by BASF) was added to the obtained mixture and dissolved, thereby obtaining a resin composition B.

<Method for Preparing Resin Composition C>

3.1 g of a compound (C-1), 0.28 g of Phosmer PP (manufactured by Unichemical Co., Ltd.), and 3.82 g of 1,6-hexanediol diacrylate (HDDA, manufactured by TOKYO CHEMICAL INDUSTRY CO., LTD.) were added to 58.9 g of a toluene dispersion liquid of ITO-1 to be dissolved. Toluene was distilled off by suction under reduced pressure while heating in a water bath at approximately 70° C. After the distillation, 0.01 g of IRGACURE 819 (manufactured by BASF) was added to the obtained mixture and dissolved, thereby obtaining a resin composition C.

Compound C-1

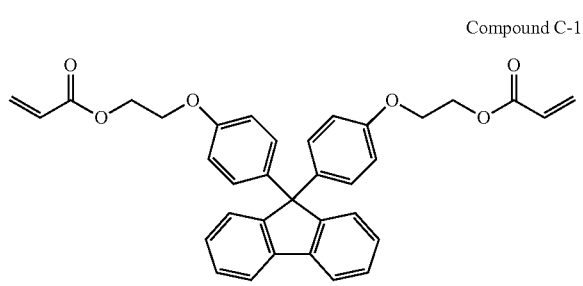 [SMILES: C=CC(=O)OCCOc1ccc(C2(c3ccc(OCCOC(=O)C=C)cc3)c3ccccc3-c3ccccc32)cc1]

<Preparation of Resin Composition 2-1>

FA-512AS (19.2 g, manufactured by Hitachi Chemical Co., Ltd.) and A9300-1CL (1.1 g, manufactured by Shin-Nakamura Chemical Co., Ltd.) were added to 55.5 g of a zirconium oxide dispersion liquid (SZR-K, manufactured by SAKAI CHEMICAL INDUSTRY CO., LTD.) and stirred until uniform. Methanol and methyl ethyl ketone (MEK) were distilled off by suction under reduced pressure while heating in a water bath at approximately 70° C. After the distillation, 0.40 g of IRGACURE 651 (manufactured by BASF) was added to the obtained mixture and dissolved, thereby preparing a resin composition 2-1. The optical characteristics of the resin composition 2-1 were (nF=1.610, vD=48.7).

<Preparation of Resin Composition 2-2>

FA-512AS (21.5 g, manufactured by Hitachi Chemical Co., Ltd.) and A9300-1CL (1.1 g, manufactured by Shin-Nakamura Chemical Co., Ltd.) were added to 48.1 g of a zirconium oxide dispersion liquid (SZR-K, manufactured by SAKAI CHEMICAL INDUSTRY CO., LID.) and stirred until uniform. Methanol and methyl ethyl ketone (MEK) were distilled off by suction under reduced pressure while heating in a water bath at approximately 70° C. After the distillation, 0.40 g of IRGACURE 651 (manufactured by BASF) was added to the obtained mixture and dissolved, thereby preparing a resin composition 2-2. The optical characteristics of the resin composition 2-2 were (nF=1.598, vD=48.1).

<Preparation of Resin Composition 2-3>

FA-512AS (20.5 g, manufactured by Hitachi Chemical Co., Ltd.) and A9 300-1CL (1.1 g, manufactured by Shin-Nakamura Chemical Co., Ltd.) were added to 51.2 g of a zirconium oxide dispersion liquid (SZR-K, manufactured by SAKAI CHEMICAL INDUSTRY CO., LTD.) and stirred until uniform. Methanol and methyl ethyl ketone (MEK) were distilled off by suction under reduced pressure while heating in a water bath at approximately 70° C. After the distillation, 0.40 g of IRGACURE 651 (manufactured by BASF) was added to the obtained mixture and dissolved, thereby preparing a resin composition 2-3. The optical characteristics of the resin composition 2-3 were (nF=1.601, vD=48.2).

<Preparation of Resin Composition 2-4>

FA-512AS (18.3 g, manufactured by Hitachi Chemical Co., Ltd.) and A9300-1CL (1.1 g, manufactured by Shin-Nakamura Chemical Co., Ltd.) were added to 58.6 g of a zirconium oxide dispersion liquid (SZR-K, manufactured by SAKAI CHEMICAL INDUSTRY CO., LID.) and stirred until uniform. Methanol and methyl ethyl ketone (MEK) were distilled off by suction under reduced pressure while heating in a water bath at approximately 70° C. After the distillation, 0.40 g of IRGACURE 651 (manufactured by BASF) was added to the obtained mixture and dissolved, thereby preparing a resin composition 2-4. The optical characteristics of the resin composition 2-4 were (nF=1.618, vD=49.1).

<Production of Cured Product of Resin Composition 1-1>

The resin composition 1-1 was sandwiched between hydrophobically treated glass plates, irradiated with UV of an exposure dose of 1.0 J/cm$^2$ (30 mW/cm$^2$) using a UV irradiation device (EXECURE 3000, manufactured by HOYA CANDEO OPTRONICS CORPORATION), and irradiated again with UV of an exposure dose of 1.0 J/cm$^2$ (5 mW/cm$^2$) to produce a cured product. The thickness of the single film was 6 μm.

<Production of Cured Products of Resin Compositions 1-2 to 1-12 and Resin Compositions A to C>

Cured products of the resin compositions 1-2 to 1-12 and the resin compositions A to C were obtained by the same method as the method for producing the cured product of the resin composition 1-1. The refractive index at wavelengths of 587.56 nm, 486.13 nm, and 656.27 nm was measured with a multi-wavelength Abbe refractometer DR-M2 (manufactured by ATAGO CO., LTD.) to determine the Abbe number vD. Table 2 shows the refractive index at a wavelength of 486.13 nm and the Abbe number vD.

<Production of Cured Product of Resin Composition 2-1>

The resin composition 2-1 was sandwiched between hydrophobically treated glass plates, irradiated with UV of an exposure dose of 2.0 J/cm$^2$ (5 mW/cm$^2$) using a UV irradiation device (EXECURE 3000, manufactured by HOYA CANDEO OPTRONICS CORPORATION) to produce a cured product. The thickness of the single film was 6 μm.

<Production of Cured Products of Resin Compositions 2-2 to 2-4>

Cured products of the resin compositions 2-2 to 2-4 were obtained by the same method as the method for producing the cured product of the resin composition 2-1.

<Transmittance Measurement>

Using the cured product of each resin composition prepared under the above-described conditions, the transmittance at a wavelength of 400 to 800 nm was measured, and the evaluation was performed based on the transmittance at 780 nm. B or more is practical. The results are shown in Table 2.

A: transmittance was 86% or more.
B: transmittance was 83% or more and less than 86%.
C: transmittance was less than 83%.

<Evaluation of Lens Diffraction Efficiency>

The refractive index of the cured products of the resin compositions 1-1 to 1-12 and the resin compositions A to C, and the resin compositions 2-1, 2-2, 2-3, and 2-4 at a wavelength of 486.13 (486) nm was measured with a multi-wavelength Abbe refractometer DR-M2 (manufactured by ATAGO CO., LTD.). Using the cured product of the resin composition of the combination shown in Table 2, the diffraction efficiency of the first-order light at a wavelength of 486 nm was calculated with reference to Equations 23 and 24 described in JP2008-241734A. It can be said that the diffraction efficiency is good in a case of being B or higher. The results are shown in Table 2.

A: diffraction efficiency was 96% or more.
B: diffraction efficiency was 93% or more and less than 96%.
C: diffraction efficiency was 90% or more and less than 93%.
D: diffraction efficiency was less than 90%.

<Production of Cured Product for Heat Cycle Test>

Each of the resin compositions 1-1 to 1-12 and the resin compositions A to C were injected into a circular mold having a diameter of 30 mm so that the thickness of the cured product was 20 μm a flat glass (BK-7) was mounted from above, and UV irradiation was performed at an exposure dose of 1.0 J/cm$^2$ (30 mW/cm$^2$) a UV irradiation device (EXECURE 3000, manufactured by HOYA CANDEO OPTRONICS CORPORATION) in an atmosphere of an oxygen concentration of 1% or less. The cured product integrated with BK-7 was released from the mold, and UV irradiation was performed again from the resin side at an exposure dose of 1.0 J/cm$^2$ (5 mW/cm$^2$).

Next, one of the resin compositions 2 shown in Table 2 and the flat glass were placed on each of the cured products, the flat glass was pressed until the thickness was 20 μm, and using the above-described UV irradiation device, UV irradiation was performed at an exposure dose of 1.0 J/cm$^2$ (5 mW/cm$^2$) to produce a cured product for a heat cycle test.

<Heat Cycle Test>

10 cured products for a heat cycle test were produced by the above-described method. The process of heating the cured product at 100° C. for 12 hours, returning to room temperature, further aging at −20° C. for 12 hours, and returning to room temperature was set as one cycle, and the process was repeated 4 times. The morphology of the test sample was observed with a digital microscope manufactured by KEYENCE CORPORATION and a laser microscope. A cured product with shape changes such as distortion, cracks, and interfacial peeling was regarded as a defective product, and a cured product without the shape changes was regarded as a non-defective product. The 10 cured products were evaluated, the ratio of non-defective products was defined as a non-defective product ratio, and the non-defective product ratio was evaluated according to the following standard. The results are shown in Table 2.

A: non-defective product ratio was 80% or more.
B: non-defective product ratio was 70% or more and less than 80%.
C: non-defective product ratio was less than 70%.

As can be seen from Table 2, the A evaluation was obtained in Examples as opposed to the C evaluation in Comparative Examples. By adding the near-ultraviolet light-absorbing organic compound (compound represented by General Formula 1), it can be estimated that the cured product of the resin composition 1 easily follows the cured product of the resin composition 2, and cracks and interfacial peeling are reduced.

TABLE 2

| | | | Example | | | | |
| --- | --- | --- | --- | --- | --- | --- | --- |
| | | | Example 1 | Example 2 | Example 3 | Example 4 | Example 5 |
| | | Resin composition | 1-1 | 1-2 | 1-3 | 1-4 | 1-5 |
| Near-ultraviolet light-absorbing organic compound | | V-3 | 31 | | | | |
| | | I-4 | | 31 | | | |
| | | III-3 | | | 31 | | |
| | | I-7 | | | | 31 | |
| | | IV-14 | | | | | 31 |
| | | IV-15 | | | | | |
| | | IV-16 | | | | | |
| | Comparative example compound | C-1 | | | | | |
| ITO | | ITO-1 | 28 | 28 | 28 | 28 | 28 |
| Dispersant | | Phosmer PP | 2.8 | 2.8 | 2.8 | 2.8 | 2.8 |
| Monomer | | HDDA | 38.2 | 38.2 | 38.2 | 38.2 | 38.2 |
| | | HDDMA | | | | | |
| Photopolymerization initiator | | Irg819 | 0.1 | 0.1 | 0.1 | 0.1 | 0.1 |
| Total | | | 100 | 100 | 100 | 100 | 100 |
| Resin composition 2 used for calculating diffraction efficiency | | | 2-1 | 2-1 | 2-1 | 2-1 | 2-1 |
| Cured product of resin composition 1 | | nF | 1.562 | 1.559 | 1.558 | 1.559 | 1.560 |
| | | vD | 21.5 | 21.4 | 21.7 | 21.2 | 20.9 |
| | Transmittance (780 nm) | | A | A | A | A | A |
| | Diffraction efficiency (486 nm) | | B | A | A | A | A |
| | Non-defective product ratio in heat cycle test | | A | A | A | A | A |

TABLE 2-continued

| | | Example 6 | Example 7 | Comparative example 1 | Comparative example 2 | Comparative example 3 |
|---|---|---|---|---|---|---|
| | Resin composition | 1-6 | 1-7 | A | B | C |
| Near-ultraviolet light-absorbing organic compound | V-3 | | | | | |
| | I-4 | | | | | |
| | III-3 | | | | | |
| | I-7 | | | | | |
| | IV-14 | | | | | |
| | IV-15 | 31 | | | | |
| | IV-16 | | 31 | | | |
| | Comparative example compound C-1 | | | | | 31 |
| ITO | ITO-1 | 28 | 28 | 43 | 28 | 28 |
| Dispersant | Phosmer PP | 2.8 | 2.8 | 4.3 | 2.8 | 2.8 |
| Monomer | HDDA | 38.2 | | 53.7 | 69.2 | 38.2 |
| | HDDMA | | 38.2 | | | |
| Photopolymerization initiator | Irg819 | 0.1 | 0.1 | 0.1 | 0.1 | 0.1 |
| Total | | 100 | 100 | 101 | 100 | 100 |
| Resin composition 2 used for calculating diffraction efficiency | | 2-1 | 2-1 | 2-2 | 2-1 | 2-1 |
| Cured product of resin composition 1 | nF | 1.560 | 1.560 | 1.550 | 1.531 | 1.548 |
| | vD | 20.6 | 20.6 | 21.2 | 30.9 | 26.8 |
| | Transmittance (780 nm) | A | A | C | A | A |
| | Diffraction efficiency (486 nm) | A | A | A | D | D |
| | Non-defective product ratio in heat cycle test | A | A | C | C | C |

| | | Example 8 | Example 9 | Example 10 | Example 11 | Example 12 |
|---|---|---|---|---|---|---|
| Resin composition | | 1-8 | 1-9 | 1-10 | 1-11 | 1-12 |
| Near-ultraviolet light-absorbing organic compound | IV-15 | 3 | 10 | 35 | 40 | 50 |
| ITO | ITO-1 | 40 | 36 | 25 | 20 | 15 |
| Dispersant | Phosmer PP | 4 | 3.6 | 2.5 | 2 | 1.5 |
| Monomer | HDDA | 53 | 50.4 | 37.5 | 38 | 33.5 |
| Photopolymerization initiator | Irg8i9 | 0.1 | 0.1 | 0.1 | 0.1 | 0.1 |
| Total | | 100 | 100 | 100 | 100 | 100 |
| Resin composition 2 used for calculating diffraction efficiency | | 2-2 | 2-3 | 2-1 | 2-1 | 2-4 |
| Cured product of resin composition 1 | nF | 1.550 | 1.551 | 1.561 | 1.560 | 1.564 |
| | vD | 21.7 | 22.0 | 20.9 | 21.5 | 21.0 |
| | Transmittance (780 nm) | B | A | A | A | A |
| | Diffraction efficiency (486 nm) | A | A | A | B | C |
| | Non-defective product ratio in heat cycle test | B | A | A | A | A |

Values in the table are % by mass.

What is claimed is:

1. A resin composition comprising:
an indium tin oxide particle; and
a near-ultraviolet light-absorbing organic compound,
wherein the near-ultraviolet light-absorbing organic compound has a first wavelength of 340 nm to 400 nm, which first shows a maximum value in a case where an absorbance is measured from a wavelength of 800 nm,
in a case where a maximum absorbance in a range of 340 nm to 400 nm is defined as Abs($\lambda$ max), an absorbance at a wavelength of 410 nm is defined as Abs(410 nm), and an absorbance at a wavelength of 430 nm is defined as Abs(430 nm), both the following two expressions are satisfied, (Abs($\lambda$ max)−Abs(410 nm))/Abs(max)≥0.97

1.00≥(Abs(max)−Abs(410 nm))/(Abs($\lambda$ max)−Abs(430 nm))≥0.97, and the near-ultraviolet light-absorbing organic compound is a compound represented by General Formula 1, $$Pol_1\text{-}Sp_1\text{-}L_1\text{-}Ar\text{-}L_2\text{-}Sp_2\text{-}Pol_2 \quad \text{(General Formula 1)}$$

in the formula, Ar is any one of aromatic ring groups represented by General Formulae 2-1 to 2-4, General Formula 2-1

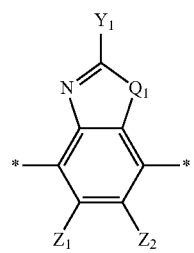

-continued

General Formula 2-2

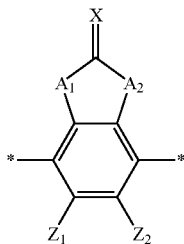

General Formula 2-3

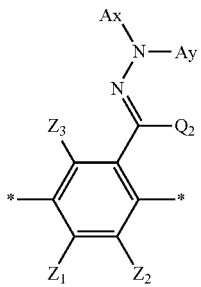

General Formula 2-4

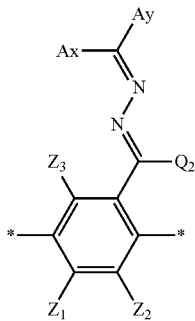

in the formulae, $Q_1$ represents —S—, —O—, or $NR_{11}$—, where $R_{11}$ represents a hydrogen atom or an alkyl group having 1 to 6 carbon atoms, $Y_1$ represents an alkyl group having 1 to 6 carbon atoms, which may have a substituent, an aromatic hydrocarbon group having 6 to 12 carbon atoms, which may have a substituent, or an aromatic heterocyclic group having 3 to 12 carbon atoms, which may have a substituent, $Z_1$, $Z_2$, and $Z_3$ each independently represent a hydrogen atom, an aliphatic hydrocarbon group having 1 to 20 carbon atoms, which may have a substituent, an alkoxy group having 1 to 20 carbon atoms, which may have a substituent, an alicyclic hydrocarbon group having 3 to 20 carbon atoms, which may have a substituent, a monovalent aromatic hydrocarbon group having 6 to 20 carbon atoms, which may have a substituent, a halogen atom, a cyano group, a nitro group, $-NR_{12}R_{13}$, or $SR_{12}$, where $Z_1$ and $Z_2$ may be bonded to each other to form an aromatic hydrocarbon ring which may have a substituent or an aromatic hetero ring which may have a substituent, and $R_{12}$ and $R_{13}$ each independently represent a hydrogen atom or an alkyl group having 1 to 6 carbon atoms, $A_1$ and $A_2$ each independently represent a group selected from the group consisting of —O—, $-NR_{21}$—, —S—, and CO—, where $R_{21}$ represents a hydrogen atom or a substituent, X represents O, S, C to which a hydrogen atom or a substituent is bonded, or N to which a hydrogen atom or a substituent is bonded, Ax represents an organic group having 1 to 30 carbon atoms, which has at least one aromatic ring selected from the group consisting of an aromatic hydrocarbon ring and an aromatic hetero ring, Ay represents a hydrogen atom, an alkyl group having 1 to 6 carbon atoms, which may have a substituent, or an organic group having 1 to 30 carbon atoms, which has at least one aromatic ring selected from the group consisting of an aromatic hydrocarbon ring and an aromatic hetero ring, where the aromatic ring included in Ax and Ay may have a substituent, and Ax and Ay may be bonded to each other to form a ring which may have a substituent, and $Q_2$ represents a hydrogen atom or an alkyl group having 1 to 6 carbon atoms, which may have a substituent, $L_1$ and $L_2$ each independently represent a single bond or a linking group selected from the group consisting of —O—, —S—, —C(=O)—, —OC(=O)—, —C(=O)O—, —OC(=O)O—, $-NR_{101}C(=O)$—, —C(=O) $NR_{102}$—, —OC(=O)$NR_{103}$—, $-NR_{104}C(=O)O$—, —SC(=O)—, and C(=O)S—, where $R_{101}$, $R_{102}$, $R_{103}$, and $R_{104}$ each independently represent $-Sp_3-Pol_3$ or a halogen atom, $Sp_1$ and $Sp_2$ each independently represent a single bond or a linking group selected from the group consisting of a linear alkylene group having 1 to 30 carbon atoms, which may have a substituent, and a group in which, in a linear alkylene group having 2 to 30 carbon atoms, which may have a substituent, one $-CH_2-$ or two or more $-CH_2-$'s not adjacent to each other are replaced with —O—, —S—, —C(=O)—, —OC(=O)—, —C(=O)O—, —OC(=O)O—, $-NR_{201}C(=O)$—, —C(=O)$NR_{202}$—, —OC(=O)$NR_{203}$—, $-NR_{204}C(=O)O$—, —SC(=O)—, or —C(=O)S—, where $R_{201}$, $R_{202}$, $R_{203}$, and $R_{204}$ each independently represent $-Sp_4-Pol_4$ or a halogen atom, and $Sp_3$ and $Sp_4$ each independently represent a single bond or a divalent linking group, and $Pol_1$, $Pol_2$, $Pol_3$, and $Pol_4$ each independently represent a hydrogen atom or a polymerizable group, where the compound represented by General Formula 1 has at least one polymerizable group.

2. The resin composition according to claim 1, wherein the following P1 in the near-ultraviolet light-absorbing organic compound is 0.005 or more, $$P1=(Abs(\lambda\ max)-Abs(410\ nm))/(410-\lambda\ max).$$

3. The resin composition according to claim 1, wherein Ar is the aromatic ring group represented by General Formula 2-2.

4. The resin composition according to claim 1, wherein both $L_1$ and $L_2$ are —O—, —OC(=O)—, —OC(=O)O—, or O—C(=O) NH—.

5. The resin composition according to claim 4, wherein both $L_1$ and $L_2$ are —O—.

6. The resin composition according to claim 1, wherein all of the polymerizable groups are (meth)acryloyloxy groups.

7. The resin composition according to claim 1, wherein any of $Pol_1$ or $Pol_2$ is a (meth)acryloyloxy group.

8. A cured product of the resin composition according to claim 1,
wherein a refractive index at a wavelength of 486.13 nm is 1.42 to 1.60, and
an Abbe number is 15 to 25.

9. A diffractive optical element comprising:
the cured product according to claim 8,
wherein the diffractive optical element includes a surface having a diffraction grating shape and formed of the cured product.

10. A multilayer diffractive optical element comprising:
a first diffractive optical element; and
a second diffractive optical element,
wherein the first diffractive optical element is the diffractive optical element according to claim 9, and
the surface of the first diffractive optical element, which has a diffraction grating shape, and a surface of the second diffractive optical element, which has a diffraction grating shape, face each other.

11. The multilayer diffractive optical element according to claim 10,
wherein a refractive index of the second diffractive optical element at a wavelength of 486.13 nm is 1.55 to 1.70, and is larger than a refractive index of the first diffractive optical element at the wavelength of 486 nm, and
an Abbe number of the second diffractive optical element is 35 to 60.

12. The multilayer diffractive optical element according to claim 10,
wherein the surface of the first diffractive optical element, which has a diffraction grating shape, and the surface of the second diffractive optical element, which has a diffraction grating shape, are in contact with each other.

13. The multilayer diffractive optical element according to claim 10, further comprising:
a transparent substrate,
wherein the first diffractive optical element, the second diffractive optical element, and the transparent substrate are arranged in this order.

14. A cured product of the resin composition according to claim 1,
wherein a refractive index at a wavelength of 486.13 nm is 1.42 to 1.60, and
an Abbe number is 15 to 25.

15. A diffractive optical element comprising:
the cured product according to claim 14,
wherein the diffractive optical element includes a surface having a diffraction grating shape and formed of the cured product.

16. A multilayer diffractive optical element comprising:
a first diffractive optical element; and
a second diffractive optical element,
wherein the first diffractive optical element is the diffractive optical element according to claim 15, and
the surface of the first diffractive optical element, which has a diffraction grating shape, and a surface of the second diffractive optical element, which has a diffraction grating shape, face each other.

17. The multilayer diffractive optical element according to claim 16,
wherein a refractive index of the second diffractive optical element at a wavelength of 486.13 nm is 1.55 to 1.70, and is larger than a refractive index of the first diffractive optical element at the wavelength of 486 nm, and
an Abbe number of the second diffractive optical element is 35 to 60.

18. The multilayer diffractive optical element according to claim 16,
wherein the surface of the first diffractive optical element, which has a diffraction grating shape, and the surface of the second diffractive optical element, which has a diffraction grating shape, are in contact with each other.

19. The multilayer diffractive optical element according to claim 16, further comprising:
a transparent substrate,
wherein the first diffractive optical element, the second diffractive optical element, and the transparent substrate are arranged in this order.

* * * * *